(12) United States Patent
Krishnamani et al.

(10) Patent No.: US 12,733,845 B2
(45) Date of Patent: Sep. 15, 2026

(54) IMPLANTABLE MICRO-ELECTROCHEMICAL CELL

(71) Applicant: Willow Laboratories, Inc., Irvine, CA (US)

(72) Inventors: Venkatramanan Krishnamani, Irvine, CA (US); Anando Devadoss, Irvine, CA (US)

(73) Assignee: Willow Laboratories, Inc., Irvine, CA (US)

( * ) Notice: Subject to any disclaimer, the term of this patent is extended or adjusted under 35 U.S.C. 154(b) by 650 days.

(21) Appl. No.: 18/050,401

(22) Filed: Oct. 27, 2022

(65) Prior Publication Data

US 2023/0145155 A1 May 11, 2023

Related U.S. Application Data

(60) Provisional application No. 63/263,284, filed on Oct. 29, 2021, provisional application No. 63/273,517, filed on Oct. 29, 2021.

(51) Int. Cl.

| | |
|---|---|
| ***A61B 5/1473*** | (2006.01) |
| ***A61B 5/00*** | (2006.01) |
| ***A61B 5/145*** | (2006.01) |
| ***A61B 5/1486*** | (2006.01) |

(52) U.S. Cl.
CPC ........ *A61B 5/1473* (2013.01); *A61B 5/14532* (2013.01); *A61B 5/14865* (2013.01); *A61B 5/4839* (2013.01); *A61B 2562/028* (2013.01)

(58) Field of Classification Search
CPC .............. A61B 5/1473; A61B 5/14532; A61B 5/14865; A61B 5/4839; A61B 2562/028
See application file for complete search history.

(56) References Cited

U.S. PATENT DOCUMENTS 3,957,612 A * 5/1976 Niedrach ........... A61B 5/14542 204/414
4,680,268 A 7/1987 Clark, Jr.
4,960,128 A 10/1990 Gordon et al.
4,964,408 A 10/1990 Hink et al.
(Continued)

FOREIGN PATENT DOCUMENTS

WO WO 2023/076992 5/2023

OTHER PUBLICATIONS

US 2022/0192529 A1, 06/2022, Al-Ali et al. (withdrawn)
(Continued)

*Primary Examiner* — Jason M Sims
*Assistant Examiner* — Kyle W. Kretzer
(74) *Attorney, Agent, or Firm* — KNOBBE, MARTENS, OLSON & BEAR, LLP

(57) ABSTRACT

A disease management system including an microelectrochemical cell configured to be implanted into a patient. The microelectrochemical cell may include a tube which may include at least one sidewall, a closed end configured to be implanted in the patient, and open end configured to receive a feedthrough for at least one electrode lead. The microelectrochemical cell may further include a fluid medium in fluid communication with bodily fluid, an analyte sensor configured to measure at least one analyte within the bodily fluid, and at least one electrical connection to the analyte sensor at the feedthrough.

19 Claims, 6 Drawing Sheets

(56) References Cited

U.S. PATENT DOCUMENTS 4,986,271 A * 1/1991 Wilkins ................ C12M 21/18 204/403.12
5,319,355 A 6/1994 Russek
5,337,744 A 8/1994 Branigan
5,341,805 A 8/1994 Stavridi et al.
D353,195 S 12/1994 Savage et al.
D353,196 S 12/1994 Savage et al.
5,377,676 A 1/1995 Vari et al.
5,387,327 A * 2/1995 Khan .................. A61B 5/1473 204/402
D359,546 S 6/1995 Savage et al.
5,431,170 A 7/1995 Mathews
5,436,499 A 7/1995 Namavar et al.
D361,840 S 8/1995 Savage et al.
D362,063 S 9/1995 Savage et al.
D363,120 S 10/1995 Savage et al.
5,456,252 A 10/1995 Vari et al.
5,479,934 A 1/1996 Imran
5,482,036 A 1/1996 Diab et al.
5,494,043 A 2/1996 O'Sullivan et al.
5,533,511 A 7/1996 Kaspari et al.
5,561,275 A 10/1996 Savage et al.
5,590,649 A 1/1997 Caro et al.
5,602,924 A 2/1997 Durand et al.
5,638,816 A 6/1997 Kiani-Azarbayjany et al.
5,638,818 A 6/1997 Diab et al.
5,645,440 A 7/1997 Tobler et al.
5,671,914 A 9/1997 Kalkhoran et al.
5,726,440 A 3/1998 Kalkhoran et al.
D393,830 S 4/1998 Tobler et al.
5,743,262 A 4/1998 Lepper, Jr. et al.
5,747,806 A 5/1998 Khalil et al.
5,750,994 A 5/1998 Schlager
5,758,644 A 6/1998 Diab et al.
5,760,910 A 6/1998 Lepper, Jr. et al.
5,890,929 A 4/1999 Mills et al.
5,919,134 A 7/1999 Diab
5,987,343 A 11/1999 Kinast
5,997,343 A 12/1999 Mills et al.
6,002,952 A 12/1999 Diab et al.
6,010,937 A 1/2000 Karam et al.
6,027,452 A 2/2000 Flaherty et al.
6,040,578 A 3/2000 Malin et al.
6,066,204 A 5/2000 Haven
6,115,673 A 9/2000 Malin et al.
6,124,597 A 9/2000 Shehada et al.
6,128,521 A 10/2000 Marro et al.
6,129,675 A 10/2000 Jay
6,144,868 A 11/2000 Parker
6,152,754 A 11/2000 Gerhardt et al.
6,184,521 B1 2/2001 Coffin, IV et al.
6,232,609 B1 5/2001 Snyder et al.
6,241,683 B1 6/2001 Macklem et al.
6,253,097 B1 6/2001 Aronow et al.
6,255,708 B1 7/2001 Sudharsanan et al.
6,259,937 B1 * 7/2001 Schulman ........... H01L 23/3107 600/377
6,280,381 B1 8/2001 Malin et al.
6,285,896 B1 9/2001 Tobler et al.
6,308,089 B1 10/2001 von der Ruhr et al.
6,317,627 B1 11/2001 Ennen et al.
6,321,100 B1 11/2001 Parker
6,334,065 B1 12/2001 Al-Ali et al.
6,360,114 B1 3/2002 Diab et al.
6,368,283 B1 4/2002 Xu et al.
6,411,373 B1 6/2002 Garside et al.
6,415,167 B1 7/2002 Blank et al.
6,430,437 B1 8/2002 Marro
6,430,525 B1 8/2002 Weber et al.
6,463,311 B1 10/2002 Diab
6,470,199 B1 10/2002 Kopotic et al.
6,487,429 B2 11/2002 Hockersmith et al.
6,505,059 B1 1/2003 Kollias et al.
6,525,386 B1 2/2003 Mills et al.
6,526,300 B1 2/2003 Kiani et al.
6,534,012 B1 3/2003 Hazen et al.
6,542,764 B1 4/2003 Al-Ali et al.
6,580,086 B1 6/2003 Schulz et al.
6,584,336 B1 6/2003 Ali et al.
6,587,196 B1 7/2003 Stippick et al.
6,587,199 B1 7/2003 Luu
6,595,316 B2 7/2003 Cybulski et al.
6,597,932 B2 7/2003 Tian et al.
6,606,511 B1 8/2003 Ali et al.
6,635,559 B2 10/2003 Greenwald et al.
6,639,668 B1 10/2003 Trepagnier
6,640,116 B2 10/2003 Diab
6,640,117 B2 10/2003 Makarewicz et al.
6,658,276 B2 12/2003 Kiani et al.
6,661,161 B1 12/2003 Lanzo et al.
6,697,656 B1 2/2004 Al-Ali
6,697,658 B2 2/2004 Ai-Ali
RE38,476 E 3/2004 Diab et al.
RE38,492 E 4/2004 Diab et al.
6,738,652 B2 5/2004 Mattu et al.
6,760,607 B2 7/2004 Al-Ali
6,788,965 B2 9/2004 Ruchti et al.
6,816,241 B2 11/2004 Grubisic
6,822,564 B2 11/2004 Al-Ali
6,850,787 B2 2/2005 Weber et al.
6,850,788 B2 2/2005 Al-Ali
6,876,931 B2 4/2005 Lorenz et al.
6,920,345 B2 7/2005 Al-Ali et al.
6,934,570 B2 8/2005 Kiani et al.
6,943,348 B1 9/2005 Coffin, IV
6,956,649 B2 10/2005 Acosta et al.
6,961,598 B2 11/2005 Diab
6,970,792 B1 11/2005 Diab
6,985,764 B2 1/2006 Mason et al.
6,990,364 B2 1/2006 Ruchti et al.
6,998,247 B2 2/2006 Monfre et al.
7,003,338 B2 2/2006 Weber et al.
7,015,451 B2 3/2006 Dalke et al.
7,027,849 B2 4/2006 Al-Ali
D526,719 S 8/2006 Richie, Jr. et al.
7,096,052 B2 8/2006 Mason et al.
7,096,054 B2 8/2006 Abdul-Hafiz et al.
D529,616 S 10/2006 Deros et al.
7,133,710 B2 11/2006 Acosta et al.
7,142,901 B2 11/2006 Kiani et al.
7,225,006 B2 5/2007 Al-Ali et al.
RE39,672 E 6/2007 Shehada et al.
7,254,429 B2 8/2007 Schurman et al.
7,254,431 B2 8/2007 Al-Ali et al.
7,254,434 B2 8/2007 Schulz et al.
7,274,955 B2 9/2007 Kiani et al.
D554,263 S 10/2007 Al-Ali et al.
7,280,858 B2 10/2007 Al-Ali et al.
7,289,835 B2 10/2007 Mansfield et al.
7,292,883 B2 11/2007 De Felice et al.
7,341,559 B2 3/2008 Schulz et al.
7,343,186 B2 3/2008 Lamego et al.
D566,282 S 4/2008 Al-Ali et al.
7,356,365 B2 4/2008 Schurman
7,371,981 B2 5/2008 Abdul-Hafiz
7,373,193 B2 5/2008 Al-Ali et al.
7,377,794 B2 5/2008 Al-Ali et al.
7,395,158 B2 7/2008 Monfre et al.
7,415,297 B2 8/2008 Al-Ali et al.
7,438,683 B2 10/2008 Al-Ali et al.
7,483,729 B2 1/2009 Al-Ali et al.
D587,657 S 3/2009 Al-Ali et al.
7,500,950 B2 3/2009 Al-Ali et al.
7,509,494 B2 3/2009 Ai-Ali
7,510,849 B2 3/2009 Schurman et al.
7,514,725 B2 4/2009 Wojtczuk et al.
7,519,406 B2 4/2009 Blank et al.
D592,507 S 5/2009 Wachman et al.
7,530,942 B1 5/2009 Diab
7,593,230 B2 9/2009 Abul-Haj et al.
7,596,398 B2 9/2009 Al-Ali et al.
7,606,608 B2 10/2009 Blank et al.
7,620,674 B2 11/2009 Ruchti et al.
D606,659 S 12/2009 Kiani et al.

(56) References Cited

U.S. PATENT DOCUMENTS 7,629,039 B2 12/2009 Eckerbom et al.
7,640,140 B2 12/2009 Ruchti et al.
7,647,083 B2 1/2010 Al-Ali et al.
D609,193 S 2/2010 Al-Ali et al.
D614,305 S 4/2010 Al-Ali et al.
7,697,966 B2 4/2010 Monfre et al.
7,698,105 B2 4/2010 Ruchti et al.
RE41,317 E 5/2010 Parker
RE41,333 E 5/2010 Blank et al.
7,729,733 B2 6/2010 Al-Ali et al.
7,761,127 B2 7/2010 Al-Ali et al.
7,764,982 B2 7/2010 Dalke et al.
D621,516 S 8/2010 Kiani et al.
7,791,155 B2 9/2010 Diab
RE41,912 E 11/2010 Parker
7,880,626 B2 2/2011 Al-Ali et al.
7,909,772 B2 3/2011 Popov et al.
7,919,713 B2 4/2011 Al-Ali et al.
7,937,128 B2 5/2011 Ai-Ali
7,937,129 B2 5/2011 Mason et al.
7,941,199 B2 5/2011 Kiani
7,957,780 B2 6/2011 Lamego et al.
7,962,188 B2 6/2011 Kiani et al.
7,976,472 B2 7/2011 Kiani
7,990,382 B2 8/2011 Kiani
8,008,088 B2 8/2011 Bellott et al.
RE42,753 E 9/2011 Kiani-Azarbayjany et al.
8,028,701 B2 10/2011 Al-Ali et al.
8,048,040 B2 11/2011 Kiani
8,050,728 B2 11/2011 Al-Ali et al.
RE43,169 E 2/2012 Parker
8,118,620 B2 2/2012 Al-Ali et al.
8,130,105 B2 3/2012 Al-Ali et al.
8,182,443 B1 5/2012 Kiani
8,190,223 B2 5/2012 Al-Ali et al.
8,203,438 B2 6/2012 Kiani et al.
8,203,704 B2 6/2012 Merritt et al.
8,219,172 B2 7/2012 Schurman et al.
8,224,411 B2 7/2012 Al-Ali et al.
8,229,532 B2 7/2012 Davis
8,233,955 B2 7/2012 Al-Ali et al.
8,255,026 B1 8/2012 Al-Ali
8,265,723 B1 9/2012 McHale et al.
8,274,360 B2 9/2012 Sampath et al.
8,280,473 B2 10/2012 Al-Ali
8,315,683 B2 11/2012 Al-Ali et al.
RE43,860 E 12/2012 Parker
8,346,330 B2 1/2013 Lamego
8,353,842 B2 1/2013 Al-Ali et al.
8,355,766 B2 1/2013 MacNeish, III et al.
8,374,665 B2 2/2013 Lamego
8,388,353 B2 3/2013 Kiani et al.
8,401,602 B2 3/2013 Kiani
8,414,499 B2 4/2013 Al-Ali et al.
8,418,524 B2 4/2013 Al-Ali
8,428,967 B2 4/2013 Olsen et al.
8,430,817 B1 4/2013 Al-Ali et al.
8,437,825 B2 5/2013 Dalvi et al.
8,455,290 B2 6/2013 Siskavich
8,457,707 B2 6/2013 Kiani
8,471,713 B2 6/2013 Poeze et al.
8,473,020 B2 6/2013 Kiani et al.
8,509,867 B2 8/2013 Workman et al.
8,515,509 B2 8/2013 Bruinsma et al.
8,523,781 B2 9/2013 Ai-Ali
D692,145 S 10/2013 Al-Ali et al.
8,571,617 B2 10/2013 Reichgott et al.
8,571,618 B1 10/2013 Lamego et al.
8,571,619 B2 10/2013 Al-Ali et al.
8,577,431 B2 11/2013 Lamego et al.
8,584,345 B2 11/2013 Al-Ali et al.
8,588,880 B2 11/2013 Abdul-Hafiz et al.
8,630,691 B2 1/2014 Lamego et al.
8,641,631 B2 2/2014 Sierra et al.
8,652,060 B2 2/2014 Al-Ali
8,666,468 B1 3/2014 Ai-Ali
8,670,811 B2 3/2014 O'Reilly
RE44,823 E 4/2014 Parker
RE44,875 E 4/2014 Kiani et al.
8,688,183 B2 4/2014 Bruinsma et al.
8,690,799 B2 4/2014 Telfort et al.
8,702,627 B2 4/2014 Telfort et al.
8,712,494 B1 4/2014 MacNeish, III et al.
8,715,206 B2 5/2014 Telfort et al.
8,723,677 B1 5/2014 Kiani
8,740,792 B1 6/2014 Kiani et al.
8,755,535 B2 6/2014 Telfort et al.
8,755,872 B1 6/2014 Marinow
8,764,671 B2 7/2014 Kiani
8,768,423 B2 7/2014 Shakespeare et al.
8,771,204 B2 7/2014 Telfort et al.
8,781,544 B2 7/2014 Al-Ali et al.
8,790,268 B2 7/2014 Al-Ali
8,801,613 B2 8/2014 Al-Ali et al.
8,821,397 B2 9/2014 Al-Ali et al.
8,821,415 B2 9/2014 Al-Ali et al.
8,830,449 B1 9/2014 Lamego et al.
8,840,549 B2 9/2014 Al-Ali et al.
8,852,094 B2 10/2014 Al-Ali et al.
8,852,994 B2 10/2014 Wojtczuk et al.
8,897,847 B2 11/2014 Al-Ali
8,911,377 B2 12/2014 Al-Ali
8,989,831 B2 3/2015 Al-Ali et al.
8,998,809 B2 4/2015 Kiani
9,066,666 B2 6/2015 Kiani
9,066,680 B1 6/2015 Al-Ali et al.
9,095,316 B2 8/2015 Welch et al.
9,106,038 B2 8/2015 Telfort et al.
9,107,625 B2 8/2015 Telfort et al.
9,131,881 B2 9/2015 Diab et al.
9,138,180 B1 9/2015 Coverston et al.
9,153,112 B1 10/2015 Kiani et al.
9,192,329 B2 11/2015 Al-Ali
9,192,351 B1 11/2015 Telfort et al.
9,195,385 B2 11/2015 Al-Ali et al.
9,211,095 B1 12/2015 Al-Ali
9,218,454 B2 12/2015 Kiani et al.
9,245,668 B1 1/2016 Vo et al.
9,267,572 B2 2/2016 Barker et al.
9,277,880 B2 3/2016 Poeze et al.
9,307,928 B1 4/2016 Al-Ali et al.
9,323,894 B2 4/2016 Kiani
D755,392 S 5/2016 Hwang et al.
9,326,712 B1 5/2016 Kiani
9,392,945 B2 7/2016 Al-Ali et al.
9,408,542 B1 8/2016 Kinast et al.
9,436,645 B2 9/2016 Al-Ali et al.
9,445,759 B1 9/2016 Lamego et al.
9,474,474 B2 10/2016 Lamego et al.
9,480,435 B2 11/2016 Olsen
9,510,779 B2 12/2016 Poeze et al.
9,517,024 B2 12/2016 Kiani et al.
9,532,722 B2 1/2017 Lamego et al.
9,560,996 B2 2/2017 Kiani
9,579,039 B2 2/2017 Jansen et al.
9,622,692 B2 4/2017 Lamego et al.
D788,312 S 5/2017 Al-Ali et al.
9,649,054 B2 5/2017 Lamego et al.
9,697,928 B2 7/2017 Al-Ali et al.
9,717,458 B2 8/2017 Lamego et al.
9,724,016 B1 8/2017 Al-Ali et al.
9,724,024 B2 8/2017 Al-Ali
9,724,025 B1 8/2017 Kiani et al.
9,749,232 B2 8/2017 Sampath et al.
9,750,442 B2 9/2017 Olsen
9,750,461 B1 9/2017 Telfort
9,775,545 B2 10/2017 Al-Ali et al.
9,778,079 B1 10/2017 Al-Ali et al.
9,782,077 B2 10/2017 Lamego et al.
9,787,568 B2 10/2017 Lamego et al.
9,808,188 B1 11/2017 Perea et al.
9,839,379 B2 12/2017 Al-Ali et al.
9,839,381 B1 12/2017 Weber et al.
9,847,749 B2 12/2017 Kiani et al.

(56) References Cited

U.S. PATENT DOCUMENTS 9,848,800 B1 12/2017 Lee et al.
9,861,298 B2 1/2018 Eckerbom et al.
9,861,305 B1 1/2018 Weber et al.
9,877,650 B2 1/2018 Muhsin et al.
9,891,079 B2 2/2018 Dalvi
9,924,897 B1 3/2018 Abdul-Hafiz
9,936,917 B2 4/2018 Poeze et al.
9,955,937 B2 5/2018 Telfort
9,965,946 B2 5/2018 Al-Ali et al.
D820,865 S 6/2018 Muhsin et al.
9,986,952 B2 6/2018 Dalvi et al.
D822,215 S 7/2018 Al-Ali et al.
D822,216 S 7/2018 Barker et al.
10,010,276 B2 7/2018 Al-Ali et al.
10,086,138 B1 10/2018 Novak, Jr.
10,111,591 B2 10/2018 Dyell et al.
D833,624 S 11/2018 DeJong et al.
10,123,729 B2 11/2018 Dyell et al.
D835,282 S 12/2018 Barker et al.
D835,283 S 12/2018 Barker et al.
D835,284 S 12/2018 Barker et al.
D835,285 S 12/2018 Barker et al.
10,149,616 B2 12/2018 Al-Ali et al.
10,154,815 B2 12/2018 Al-Ali et al.
10,159,412 B2 12/2018 Lamego et al.
10,188,348 B2 1/2019 Al-Ali et al.
RE47,218 E 2/2019 Al-Ali
RE47,244 E 2/2019 Kiani et al.
RE47,249 E 2/2019 Kiani et al.
10,205,291 B2 2/2019 Scruggs et al.
10,226,187 B2 3/2019 Al-Ali et al.
10,231,657 B2 3/2019 Al-Ali et al.
10,231,670 B2 3/2019 Blank et al.
RE47,353 E 4/2019 Kiani et al.
10,279,247 B2 5/2019 Kiani
10,292,664 B2 5/2019 Al-Ali
10,299,720 B2 5/2019 Brown et al.
10,327,337 B2 6/2019 Schmidt et al.
10,327,713 B2 6/2019 Barker et al.
10,332,630 B2 6/2019 Al-Ali
10,383,520 B2 8/2019 Wojtczuk et al.
10,383,527 B2 8/2019 Al-Ali
10,388,120 B2 8/2019 Muhsin et al.
D864,120 S 10/2019 Forrest et al.
10,441,181 B1 10/2019 Telfort et al.
10,441,196 B2 10/2019 Eckerbom et al.
10,448,844 B2 10/2019 Al-Ali et al.
10,448,871 B2 10/2019 Al-Ali et al.
10,456,038 B2 10/2019 Lamego et al.
10,463,340 B2 11/2019 Telfort et al.
10,471,159 B1 11/2019 Lapotko et al.
10,505,311 B2 12/2019 Al-Ali et al.
10,524,738 B2 1/2020 Olsen
10,532,174 B2 1/2020 Al-Ali
10,537,285 B2 1/2020 Shreim et al.
10,542,903 B2 1/2020 Al-Ali et al.
10,555,678 B2 2/2020 Dalvi et al.
10,568,553 B2 2/2020 O'Neil et al.
10,608,817 B2 3/2020 Haider et al.
D880,477 S 4/2020 Forrest et al.
10,617,302 B2 4/2020 Al-Ali et al.
10,617,335 B2 4/2020 Al-Ali et al.
10,637,181 B2 4/2020 Al-Ali et al.
D886,849 S 6/2020 Muhsin et al.
D887,548 S 6/2020 Abdul-Hafiz et al.
D887,549 S 6/2020 Abdul-Hafiz et al.
10,667,764 B2 6/2020 Ahmed et al.
D890,708 S 7/2020 Forrest et al.
10,721,785 B2 7/2020 Al-Ali
10,736,518 B2 8/2020 Al-Ali et al.
10,750,984 B2 8/2020 Pauley et al.
D897,098 S 9/2020 Al-Ali
10,779,098 B2 9/2020 Iswanto et al.
10,827,961 B1 11/2020 Iyengar et al.
10,828,007 B1 11/2020 Telfort et al.
10,832,818 B2 11/2020 Muhsin et al.
10,849,554 B2 12/2020 Shreim et al.
10,856,750 B2 12/2020 Indorf
D906,970 S 1/2021 Forrest et al.
D908,213 S 1/2021 Abdul-Hafiz et al.
10,918,281 B2 2/2021 Al-Ali et al.
10,932,705 B2 3/2021 Muhsin et al.
10,932,729 B2 3/2021 Kiani et al.
10,939,878 B2 3/2021 Kiani et al.
10,956,950 B2 3/2021 Al-Ali et al.
D916,135 S 4/2021 Indorf et al.
D917,046 S 4/2021 Abdul-Hafiz et al.
D917,550 S 4/2021 Indorf et al.
D917,564 S 4/2021 Indorf et al.
D917,704 S 4/2021 Al-Ali et al.
10,987,066 B2 4/2021 Chandran et al.
10,991,135 B2 4/2021 Al-Ali et al.
D919,094 S 5/2021 Al-Ali et al.
D919,100 S 5/2021 Al-Ali et al.
11,006,867 B2 5/2021 Al-Ali
D921,202 S 6/2021 Al-Ali et al.
11,024,064 B2 6/2021 Muhsin et al.
11,026,604 B2 6/2021 Chen et al.
D925,597 S 7/2021 Chandran et al.
D927,699 S 8/2021 Al-Ali et al.
11,076,777 B2 8/2021 Lee et al.
11,114,188 B2 9/2021 Poeze et al.
D933,232 S 10/2021 Al-Ali et al.
D933,233 S 10/2021 Al-Ali et al.
D933,234 S 10/2021 Al-Ali et al.
11,145,408 B2 10/2021 Sampath et al.
11,147,518 B1 10/2021 Al-Ali et al.
11,185,262 B2 11/2021 Al-Ali et al.
11,191,484 B2 12/2021 Kiani et al.
D946,596 S 3/2022 Ahmed
D946,597 S 3/2022 Ahmed
D946,598 S 3/2022 Ahmed
D946,617 S 3/2022 Ahmed
11,272,839 B2 3/2022 Al-Ali et al.
11,289,199 B2 3/2022 Al-Ali
RE49,034 E 4/2022 Ai-Ali
11,298,021 B2 4/2022 Muhsin et al.
D950,580 S 5/2022 Ahmed
D950,599 S 5/2022 Ahmed
D950,738 S 5/2022 Al-Ali et al.
D957,648 S 7/2022 Al-Ali
11,382,567 B2 7/2022 O'Brien et al.
11,389,093 B2 7/2022 Triman et al.
11,406,286 B2 8/2022 Al-Ali et al.
11,417,426 B2 8/2022 Muhsin et al.
11,439,329 B2 9/2022 Lamego
11,445,948 B2 9/2022 Scruggs et al.
D965,789 S 10/2022 Al-Ali et al.
D967,433 S 10/2022 Al-Ali et al.
11,464,410 B2 10/2022 Muhsin
11,504,058 B1 11/2022 Sharma et al.
11,504,066 B1 11/2022 Dalvi et al.
D971,933 S 12/2022 Ahmed
D973,072 S 12/2022 Ahmed
D973,685 S 12/2022 Ahmed
D973,686 S 12/2022 Ahmed
D974,193 S 1/2023 Forrest et al.
D979,516 S 2/2023 Al-Ali et al.
D980,091 S 3/2023 Forrest et al.
11,596,363 B2 3/2023 Lamego
11,627,919 B2 4/2023 Kiani et al.
11,637,437 B2 4/2023 Al-Ali et al.
D985,498 S 5/2023 Al-Ali et al.
11,653,862 B2 5/2023 Dalvi et al.
D989,112 S 6/2023 Muhsin et al.
D989,327 S 6/2023 Al-Ali et al.
11,678,829 B2 6/2023 Al-Ali et al.
11,679,579 B2 6/2023 Al-Ali
11,684,296 B2 6/2023 Vo et al.
11,692,934 B2 7/2023 Normand et al.
11,701,043 B2 7/2023 Al-Ali et al.
D997,365 S 8/2023 Hwang
11,721,105 B2 8/2023 Ranasinghe et al.
11,730,379 B2 8/2023 Ahmed et al.

(56) References Cited

U.S. PATENT DOCUMENTS

D998,625 S 9/2023 Indorf et al.
D998,630 S 9/2023 Indorf et al.
D998,631 S 9/2023 Indorf et al.
D999,244 S 9/2023 Indorf et al.
D999,245 S 9/2023 Indorf et al.
D999,246 S 9/2023 Indorf et al.
11,766,198 B2 9/2023 Pauley et al.
D1,000,975 S 10/2023 Al-Ali et al.
11,803,623 B2 10/2023 Kiani et al.
11,832,940 B2 12/2023 Diab et al.
D1,013,179 S 1/2024 Al-Ali et al.
11,872,156 B2 1/2024 Telfort et al.
11,879,960 B2 1/2024 Ranasinghe et al.
11,883,129 B2 1/2024 Olsen
D1,022,729 S 4/2024 Forrest et al.
11,951,186 B2 4/2024 Krishnamani et al.
11,974,833 B2 5/2024 Forrest et al.
11,986,067 B2 5/2024 Al-Ali et al.
11,986,289 B2 5/2024 Dalvi et al.
11,986,305 B2 5/2024 Al-Ali et al.
D1,031,729 S 6/2024 Forrest et al.
12,004,869 B2 6/2024 Kiani et al.
12,014,328 B2 6/2024 Wachman et al.
D1,036,293 S 7/2024 Al-Ali et al.
D1,037,462 S 7/2024 Al-Ali et al.
12,029,844 B2 7/2024 Pauley et al.
12,048,534 B2 7/2024 Vo et al.
12,064,217 B2 8/2024 Ahmed et al.
12,066,426 B1 8/2024 Lapotko et al.
D1,041,511 S 9/2024 Indorf et al.
D1,042,596 S 9/2024 DeJong et al.
D1,042,852 S 9/2024 Hwang
12,076,159 B2 9/2024 Belur Nagaraj et al.
12,082,926 B2 9/2024 Sharma et al.
D1,044,828 S 10/2024 Chandran et al.
D1,048,571 S 10/2024 Yu et al.
D1,048,908 S 10/2024 Al-Ali et al.
12,106,752 B2 10/2024 Campbell et al.
12,114,974 B2 10/2024 Al-Ali et al.
12,126,683 B2 10/2024 Koo et al.
12,127,838 B2 10/2024 Olsen et al.
12,128,213 B2 10/2024 Kiani et al.
12,131,661 B2 10/2024 Pauley et al.
D1,050,910 S 11/2024 Al-Ali et al.
12,178,572 B1 12/2024 Pauley et al.
12,178,581 B2 12/2024 Telfort et al.
12,178,852 B2 12/2024 Kiani et al.
D1,057,159 S 1/2025 DeJong et al.
D1,057,160 S 1/2025 DeJong et al.
12,198,790 B1 1/2025 Al-Ali
12,200,421 B2 1/2025 Campbell et al.
12,207,901 B1 1/2025 Lapotko et al.
D1,060,680 S 2/2025 Al-Ali et al.
D1,061,585 S 2/2025 Indorf
D1,063,893 S 2/2025 DeJong et al.
12,220,207 B2 2/2025 Telfort et al.
12,235,941 B2 2/2025 Kiani et al.
12,236,767 B2 2/2025 Muhsin
D1,066,244 S 3/2025 Lim et al.
D1,066,672 S 3/2025 Al-Ali et al.
D1,068,656 S 4/2025 Trevisan et al.
D1,071,195 S 4/2025 Seung
D1,072,836 S 4/2025 Indorf
D1,072,837 S 4/2025 Ahmed et al.
12,272,445 B1 4/2025 Kiani
D1,078,689 S 6/2025 Hwang
D1,079,020 S 6/2025 Hwang
12,336,796 B2 6/2025 Al-Ali
D1,083,653 S 7/2025 DeJong et al.
D1,085,102 S 7/2025 Indorf et al.
12,362,596 B2 7/2025 Barker et al.
12,390,114 B2 8/2025 Novak, Jr. et al.
D1,092,244 S 9/2025 DeJong et al.
D1,093,406 S 9/2025 Indorf et al.
D1,094,735 S 9/2025 DeJong et al.
D1,095,288 S 9/2025 Lim
D1,095,483 S 9/2025 DeJong et al.
12,433,524 B2 10/2025 Al-Ali et al.
12,440,128 B2 10/2025 Al-Ali et al.
2001/0034477 A1 10/2001 Mansfield et al.
2001/0039483 A1 11/2001 Brand et al.
2002/0010401 A1 1/2002 Bushmakin et al.
2002/0058864 A1 5/2002 Mansfield et al.
2002/0133080 A1 9/2002 Apruzzese et al.
2003/0013975 A1 1/2003 Kiani
2003/0018243 A1 1/2003 Gerhardt et al.
2003/0042137 A1* 3/2003 Mao ...................... C12Q 1/002 204/415
2003/0144582 A1 7/2003 Cohen et al.
2003/0156288 A1 8/2003 Barnum et al.
2003/0212312 A1 11/2003 Coffin, IV et al.
2004/0106163 A1 6/2004 Workman, Jr. et al.
2005/0055276 A1 3/2005 Kiani et al.
2005/0234317 A1 10/2005 Kiani
2006/0073719 A1 4/2006 Kiani
2006/0189871 A1 8/2006 Al-Ali et al.
2007/0073116 A1 3/2007 Kiani et al.
2007/0180140 A1 8/2007 Welch et al.
2007/0244377 A1 10/2007 Cozad et al.
2008/0064965 A1 3/2008 Jay et al.
2008/0094228 A1 4/2008 Welch et al.
2008/0103375 A1 5/2008 Kiani
2008/0214914 A1* 9/2008 Say ...................... A61B 5/1451 427/2.12
2008/0214916 A1* 9/2008 Yodfat ............... A61B 5/14532 600/347
2008/0221418 A1 9/2008 Al-Ali et al.
2009/0036759 A1 2/2009 Ault et al.
2009/0093687 A1 4/2009 Telfort et al.
2009/0095926 A1 4/2009 MacNeish, III
2009/0247984 A1 10/2009 Lamego et al.
2009/0275844 A1 11/2009 Ai-Ali
2010/0004518 A1 1/2010 Vo et al.
2010/0030040 A1 2/2010 Poeze et al.
2010/0099964 A1 4/2010 O'Reilly et al.
2010/0234718 A1 9/2010 Sampath et al.
2010/0270257 A1 10/2010 Wachman et al.
2011/0028806 A1 2/2011 Merritt et al.
2011/0028809 A1 2/2011 Goodman
2011/0040197 A1 2/2011 Welch et al.
2011/0082711 A1 4/2011 Poeze et al.
2011/0087081 A1 4/2011 Kiani et al.
2011/0118561 A1 5/2011 Tari et al.
2011/0137297 A1 6/2011 Kiani et al.
2011/0172498 A1 7/2011 Olsen et al.
2012/0123231 A1 5/2012 O'Reilly
2012/0165629 A1 6/2012 Merritt et al.
2012/0209084 A1 8/2012 Olsen et al.
2012/0226117 A1 9/2012 Lamego et al.
2012/0283524 A1 11/2012 Kiani et al.
2013/0023775 A1 1/2013 Lamego et al.
2013/0060147 A1 3/2013 Welch et al.
2013/0096405 A1 4/2013 Garfio
2013/0296672 A1 11/2013 O'Neil et al.
2013/0345921 A1 12/2013 Al-Ali et al.
2014/0166076 A1 6/2014 Kiani et al.
2014/0180160 A1 6/2014 Brown et al.
2014/0187973 A1 7/2014 Brown et al.
2014/0275871 A1 9/2014 Lamego et al.
2014/0275872 A1 9/2014 Merritt et al.
2014/0316217 A1 10/2014 Purdon et al.
2014/0316218 A1 10/2014 Purdon et al.
2014/0323897 A1 10/2014 Brown et al.
2014/0323898 A1 10/2014 Purdon et al.
2015/0005600 A1 1/2015 Blank et al.
2015/0011907 A1 1/2015 Purdon et al.
2015/0073241 A1 3/2015 Lamego
2015/0080754 A1 3/2015 Purdon et al.
2015/0099950 A1 4/2015 Al-Ali et al.
2016/0196388 A1 7/2016 Lamego
2016/0367173 A1 12/2016 Dalvi et al.
2017/0024748 A1 1/2017 Haider
2017/0173632 A1 6/2017 Ai-Ai
2017/0251974 A1 9/2017 Shreim et al.

(56) References Cited

U.S. PATENT DOCUMENTS

2018/0242926 A1 8/2018 Muhsin et al.
2018/0247712 A1 8/2018 Muhsin et al.
2019/0239787 A1 8/2019 Pauley et al.
2019/0320906 A1 10/2019 Olsen
2019/0374713 A1 12/2019 Kiani et al.
2020/0060869 A1 2/2020 Telfort et al.
2020/0111552 A1 4/2020 Ahmed
2020/0113520 A1 4/2020 Abdul-Hafiz et al.
2020/0138368 A1 5/2020 Kiani et al.
2020/0163597 A1 5/2020 Dalvi et al.
2020/0196877 A1 6/2020 Vo et al.
2020/0253474 A1 8/2020 Muhsin et al.
2020/0253544 A1 8/2020 Belur Nagaraj et al.
2020/0275841 A1 9/2020 Telfort et al.
2020/0288983 A1 9/2020 Telfort et al.
2020/0321793 A1 10/2020 Al-Ali et al.
2020/0329983 A1 10/2020 Al-Ali et al.
2020/0329984 A1 10/2020 Al-Ali et al.
2020/0329993 A1 10/2020 Al-Ali et al.
2020/0330037 A1 10/2020 Al-Ali et al.
2021/0022628 A1 1/2021 Telfort et al.
2021/0104173 A1 4/2021 Pauley et al.
2021/0113121 A1 4/2021 Diab et al.
2021/0117525 A1 4/2021 Kiani et al.
2021/0118581 A1 4/2021 Kiani et al.
2021/0121582 A1 4/2021 Krishnamani et al.
2021/0161465 A1 6/2021 Barker et al.
2021/0236729 A1 8/2021 Kiani et al.
2021/0256267 A1 8/2021 Ranasinghe et al.
2021/0256835 A1 8/2021 Ranasinghe et al.
2021/0275101 A1 9/2021 Vo et al.
2021/0290060 A1 9/2021 Ahmed
2021/0290072 A1 9/2021 Forrest
2021/0290080 A1 9/2021 Ahmed
2021/0290120 A1 9/2021 Ai-Ali
2021/0290177 A1 9/2021 Novak, Jr.
2021/0290184 A1 9/2021 Ahmed
2021/0296008 A1 9/2021 Novak, Jr.
2021/0330228 A1 10/2021 Olsen et al.
2021/0386382 A1 12/2021 Olsen et al.
2021/0402110 A1 12/2021 Pauley et al.
2022/0026355 A1 1/2022 Normand et al.
2022/0039707 A1 2/2022 Sharma et al.
2022/0053892 A1 2/2022 Al-Ali et al.
2022/0071562 A1 3/2022 Kiani
2022/0096603 A1 3/2022 Kiani et al.
2022/0151521 A1 5/2022 Krishnamani et al.
2022/0218244 A1 7/2022 Kiani et al.
2022/0287574 A1 9/2022 Telfort et al.
2022/0296161 A1 9/2022 Al-Ali et al.
2022/0361819 A1 11/2022 Al-Ali et al.
2022/0379059 A1 12/2022 Yu et al.
2022/0392610 A1 12/2022 Kiani et al.
2023/0028745 A1 1/2023 Al-Ali
2023/0038389 A1 2/2023 Vo
2023/0045647 A1 2/2023 Vo
2023/0058052 A1 2/2023 Ai-Ali
2023/0058342 A1 2/2023 Kiani
2023/0069789 A1 3/2023 Koo et al.
2023/0087671 A1 3/2023 Telfort et al.
2023/0110152 A1 4/2023 Forrest et al.
2023/0111198 A1 4/2023 Yu et al.
2023/0115397 A1 4/2023 Vo et al.
2023/0116371 A1 4/2023 Mills et al.
2023/0135297 A1 5/2023 Kiani et al.
2023/0138098 A1 5/2023 Telfort et al.
2023/0147750 A1 5/2023 Barker et al.
2023/0210417 A1 7/2023 Al-Ali et al.
2023/0222805 A1 7/2023 Muhsin et al.
2023/0222887 A1 7/2023 Muhsin et al.
2023/0226331 A1 7/2023 Kiani et al.
2023/0284916 A1 9/2023 Telfort
2023/0284943 A1 9/2023 Scruggs et al.
2023/0301562 A1 9/2023 Scruggs et al.
2023/0346993 A1 11/2023 Kiani et al.
2023/0368221 A1 11/2023 Haider
2023/0371893 A1 11/2023 Al-Ali et al.
2023/0389837 A1 12/2023 Krishnamani et al.
2024/0016418 A1 1/2024 Devadoss et al.
2024/0016419 A1 1/2024 Devadoss et al.
2024/0047061 A1 2/2024 Al-Ali et al.
2024/0049310 A1 2/2024 Al-Ali et al.
2024/0049986 A1 2/2024 Al-Ali et al.
2024/0081656 A1 3/2024 DeJong et al.
2024/0122486 A1 4/2024 Kiani
2024/0180456 A1 6/2024 Al-Ali
2024/0188872 A1 6/2024 Al-Ali et al.
2024/0245855 A1 7/2024 Vo et al.
2024/0260894 A1 8/2024 Olsen
2024/0267698 A1 8/2024 Telfort et al.
2024/0277233 A1 8/2024 Al-Ali
2024/0277280 A1 8/2024 Al-Ali
2024/0298920 A1 9/2024 Fernkbist et al.
2024/0306985 A1 9/2024 Vo et al.
2024/0324953 A1 10/2024 Telfort
2024/0380246 A1 11/2024 Moran
2024/0380247 A1 11/2024 Moran
2024/0404549 A1 12/2024 Campbell et al.
2025/0000458 A1 1/2025 Abdul-Hafiz et al.
2025/0037836 A1 1/2025 Kiani
2025/0100482 A1 3/2025 Al-Ali et al.
2025/0118415 A1 4/2025 Olsen
2025/0255764 A1 8/2025 Stead
2025/0278512 A1 9/2025 Koo et al.
2025/0281059 A1 9/2025 Avendano
2025/0288250 A1 9/2025 Al-Ali et al.
2025/0295366 A1 9/2025 Al-Ali et al.
2025/0302426 A1 10/2025 Ha et al.
2025/0311949 A1 10/2025 Al-Ali et al.

OTHER PUBLICATIONS

US 2024/0016391 A1, 01/2024, Lapotko et al. (withdrawn)
Invitation to Pay Fees received in PCT Application No. PCT/US2022/078773, dated Feb. 22, 2023 in 14 pages.
International Search Report and Written Opinion received in PCT Application No. PCT/US2022/078773, dated Apr. 14, 2023 in 19 pages.

* cited by examiner

IMPLANTABLE MICRO-ELECTROCHEMICAL CELL

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. For example, this application claims priority to U.S. Provisional Application No. 63/273,517 and U.S. Provisional Application No. 63/263,284, the entire content of which is incorporated by reference herein in its entirety and for all purposes and forms a part of this specification.

BACKGROUND

Field

The general field of this disclosure is glucose sensing and disease management systems.

Description

Diabetes is a chronic disease that impacts many individuals, both adults and children. The management of diabetes may include the measurement of glucose within the interstitial space including blood and/or interstitial fluid of a patient and administration of insulin to the patient. A closed loop insulin administration system includes both a sensor to take glucose measurements from the interstitial space including blood and/or interstitial fluid of the patient and an insulin administration device which administers insulin to the patient based on the glucose measurements. Closed loop insulin administration systems allow individuals impacted by diabetes to go about daily life with much less worry about their insulin or glucose levels which can vastly improve a diabetic's quality of life.

SUMMARY

Various aspects of systems, methods and devices within the scope of the appended claims each have several aspects, no single one of which is solely responsible for the desirable attributes described herein. Without limiting the scope of the appended claims, some prominent features are described herein.

In some aspects, a disease management device can include an implantable micro-electrochemical cell. In some aspects, the implantable micro-electrochemical cell may include a tube configured to be implanted in a tissue site of a patient, the tube comprising: at least one sidewall; a closed end configured to be implanted in the patient; an open end configured to receive a feedthrough for at least one electrode lead; a seal configured to seal the open end of the tube; wherein the at least one sidewall comprises at least one porous interface; a fluid medium configured to be in fluid communication with bodily fluid at a tissue site of the patient through at least one porous interface; an analyte sensor in fluid communication with the fluid medium and configured to measure at least one analyte from the bodily fluid; and at least one electrical connection to the analyte sensor at the feedthrough.

In some examples, the porous interface may serve as a medium between surrounding electrodes. Additionally, in some examples, the porous interface contains a cross-linked water absorbing polymer matrix that may further include a hydrogel formed by cross-linking polyethylene glycol diglycidyl ether and polyethlene glycol diamine. In some examples, the tube may include an outer diameter of 300 micrometers and an inner diameter of 250 micrometers. Furthermore, in some examples, the tube may be formed with a mold and polymer resin. In some examples, the porous interface may include a diameter that ranges between 10-50 micrometers. Furthermore, in some examples, the porous interface may be created by laser drilling the tube.

In some examples, the analyte electrode may have a diameter of 100 micrometers, an insulting layer with a thickness of 15 micrometers, and a top modified with a suitable sensing element. In some examples, the tip of the analyte electrode may be immersed in the cross-linked water absorbing polymer matrix, In some examples, the sensing element may include an enzyme. Furthermore, in some examples, at least one electrode lead is complimented by a reference electrode and a counter electrode that is immersed in the cross-linked water absorbing polymer matrix. In some examples, the reference electrode may include Ag/AgCl and have a diameter of 20 micrometers. In some examples, the counter electrode may include Pt wire and have a diameter of 20 micrometers. In some examples, the electrode leads are sealed with a polymer resin such that an inner side of the tube is isolated from the electrode leads.

BRIEF DESCRIPTION OF THE DRAWINGS

These and other features, aspects, and advantages of the present application are described with reference to drawings of certain aspects, which are intended to illustrate, but not limit, the present disclosure. It is to be understood that the attached drawings are for the purpose of illustrating concepts disclosed in the present application and may not be to scale.

DETAILED DESCRIPTION

Although certain preferred aspects and examples are disclosed below, inventive subject matter extends beyond the specifically disclosed embodiments to other alternative aspects and/or uses and to modifications and equivalents thereof. Thus, the scope of the claims that may arise here from is not limited by any of the particular aspects described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various aspects, certain aspects and advantages of these aspects are described. Not necessarily all such aspects or advantages are achieved by any particular aspect. Thus, for example, various aspects may be carried out in a manner that achieves or optimizes one advantage or group of advantages as taught herein without necessarily achieving other aspects or advantages as may also be taught or suggested herein.

Figure 1:
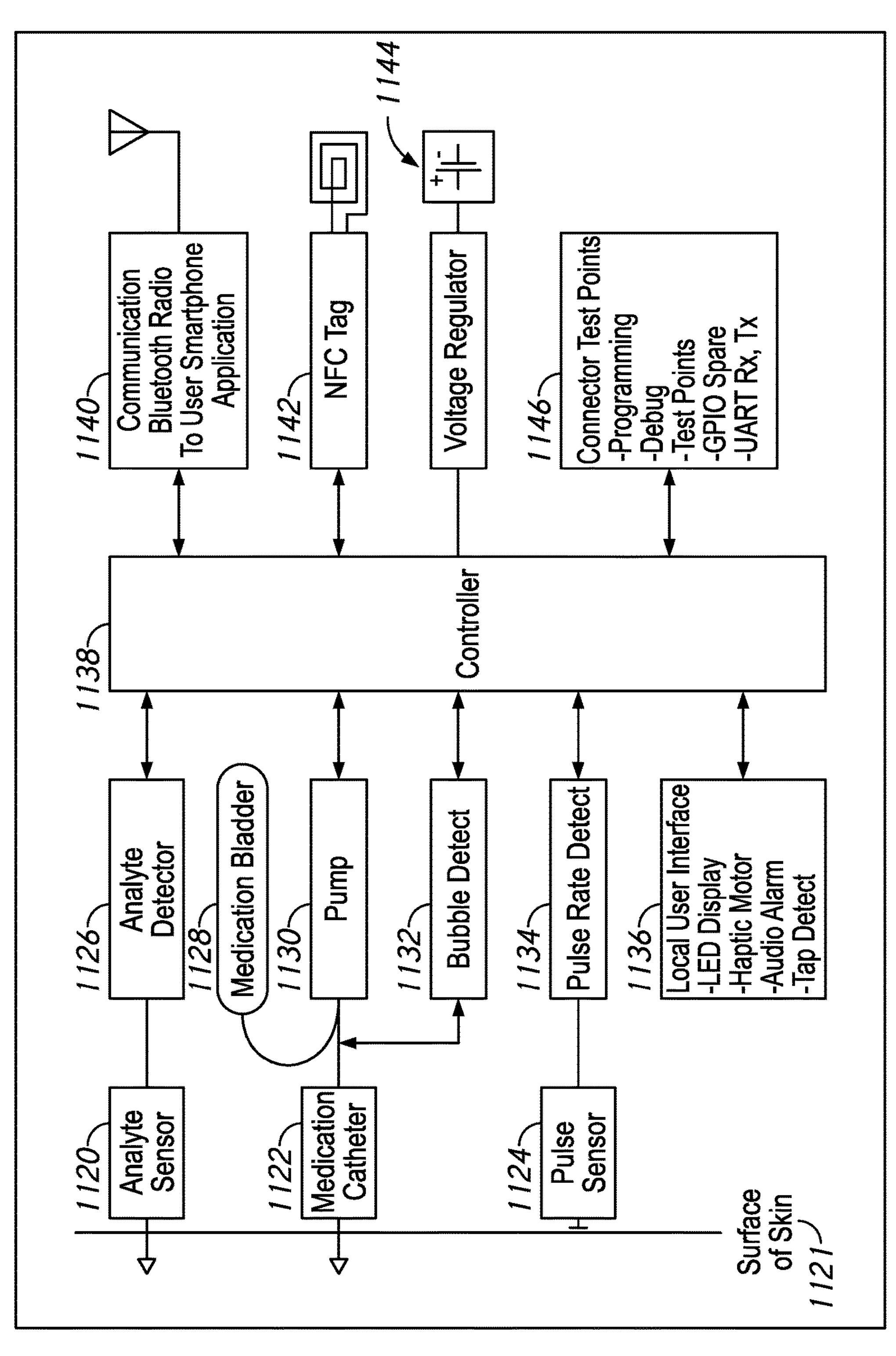
FIG. 1 illustrates an example disease management system that may be part of a disease management environment or used as an interleaved device.

FIG. 1 shows a block diagram of an example disease management system 1101. In some examples, the disease management system 1101 may be part of a disease management environment, such as described above. A disease management system 1101 may be configured to measure one or more physiological parameters of a patient (such as pulse, skin temperature, or other values), measure one or more analytes present in the blood of a patient (such as glucose, lipids, or other analyte) and administer medication (such as insulin, glucagon, or other medication). In some examples, a disease management system 1101 may be configured to communicate with one or more hardware processors that may be external to the disease management system 1101, such as a cloud based processor or user device. A disease management system 1101 may include an NFC tag to support authentication and pairing with a user device (for example, smart phone or smart watch), Bluetooth communication with additional disease management systems or devices, and Bluetooth communication with a paired user device running an associated control application. To support ease of use and safe interaction with the patient, the system may incorporate user input through a tap-detecting accelerometer and provide feedback via an audio speaker, haptic vibration, and/or optical indicators. The system may operate on battery power and support both shelf-life and reliable operation once applied to the patient. Battery life may be managed through control of several planned levels of sleep and power consumption. To support this reliability, a controller can monitor several system-health parameters, and monitor temperatures of the included medication, and ambient temperature for the life of the device.

As illustrated in FIG. 1, a controller 1138 of the disease management system 1101 may be configured to communicate and control one or more components of the disease management system 1101. The controller 1138 may include one or more hardware processors, such as a printed circuit board (PCB) or the like. The controller 1138 may be configured to communicate with peripheral devices or components to support the accurate measurement of physiological parameters and blood analytes, such as patient pulse, temperature, and blood glucose, using detector electronics. The controller 1138 may subsequently calculate dose or receive a calculated dose value and administer medication, such as insulin, by actuation of an actuated pump. The controller 1138 may record device activity and transfer the recorded data to non-volatile secure memory space. At the end of the life of a device or system, the controller can be configured to lock operation, and create a data recovery module to permit authenticated access to the recorded data if needed.

A disease management system 1101 may include an analyte sensor 1120. The analyte sensor 1120 may be configured to detect analytes in the patient's blood. For example, an analyte sensor 1120 can include a glucose sensing probe configured to pierce the surface of the skin 1121. In some examples, a disease management system 1101 may include a plurality of analyte sensors 1120 to detect one or more analytes. In some examples, an analyte sensor 1120 may be configured to detect a plurality of analytes. Sensed analytes may include, but are not limited to, glucose, insulin, and other analytes. An analyte sensor 1120 may be configured to communicate with an analyte detector 1126. The analyte detector 1126 may be configured to receive a signal of one or more analyte sensors 1120 in order to measure one or more analytes in the blood of the patient. The analyte detector 1126 may be configured to communicate with the controller 1138. For example, the analyte detector 1126 may be configured to, for example, send analyte values to the controller 1138 and receive control signals from the controller.

A disease management system 1101 may include a medication catheter 1122. The medication catheter 1122 may be configured to administer medication, including, but not limited to insulin, to the patient. The medication catheter 1122 may receive medication from a medication bladder 1128 configured to contain medication to be administered. The medication bladder 1128 may be configured to contain medication for a prolonged period, such as 1 day, 3 days, 6 days, or more. The medication bladder 1128 may be configured to contain certain medication types, such as insulin. In some examples, a disease management system 1101 may include a plurality of medication bladders 1128 for one or more reservoirs of the same or different medications. In some examples, a disease management system 1101 may be configured to mix medications from medication bladders 1128 prior to administration to the patient. A pump 1130 may be configured to cause medication to be administered from the bladder 1128 to the patient through the insulin catheter 1122. A pump 1130 may include, but is not limited to, a pump such as described herein.

A disease management system 1101 may optionally include a physiological sensor 1124. The physiological sensor 1124 may include a pulse rate sensor, temperature sensor, pulse oximeter, the like or a combination thereof. In some examples, a disease management system 1101 may be configured to include a plurality of physiological sensors. The physiological sensor 1124 may be configured to communicate with a physiological detector 1134. The physiological detector 1134 may be configured to receive a signals of the physiological sensor 1124. The physiological detector 1134 may be configured to measure or determine and communicate a physiological value from the signal. The physiological detector 1134 may be configured to communicate with the controller 1138. For example, the physiological detector 1134 may be configured to, for example, send measured physiological values to the controller 1138 and receive control signals from the controller.

A disease management system 1101 may include one or more local user interfacing components 1136. For example, a local user interfacing component 1136 may include, but is not limited to one or more optical displays, haptic motors, audio speakers, and user input detectors. In some examples, an optical display may include an LED light configured to display a plurality of colors. In some examples, an optical display may include a digital display of information associated with the disease management system 1101, including, but not limited to, device status, medication status, patient status, measured analyte or physiological values, the like or a combination thereof. In some examples, a user input detector may include an inertial measurement unit, tap detector, touch display, or other component configured to accept and receive user input. In some examples, audio speakers may be configured to communicate audible alarms related to device status, medication status user status, the like or a combination thereof. A controller 1138 may be configured to communicate with the one or more local interfacing components 1136 by, for example, receiving user input from the one or more user input components or sending control signals to, for example, activate a haptic motor, generate an output to the optical display, generate an audible output, or otherwise control one or more of the local user interfacing components 1136.

A disease management system 1101 may include one or more communication components 1140. A communication component 1140 can include, but is not limited to one or more radios configured to emit Bluetooth, cellular, Wi-Fi, or other wireless signals. In some examples, a communication component 1140 can include a port for a wired connection. Additionally, a disease management system 1101 may include an NFC tag 1142 to facilitate in communicating with one or more hardware processors. The one or more communication components 1140 and NFC tag 1142 may be configured to communicate with the controller 1138 in order to send and/or receive information associated with the disease management system 1101. For example, a controller 1138 may communicate medication information and measured values through the one or more communication components 1140 to an external device. Additionally, the controller 1138 may receive instructions associated with measurement sampling rates, medication delivery, or other information associated with operation of the management system 1101 through the one or more communication components 1140 from one or more external devices.

A disease management system 1101 may include one or more power components 1144. The power components may include, but are not limited to one or more batteries and power management components, such as a voltage regulator. Power from the one or more power components 1144 may be accessed by the controller and/or other components of the disease management system 1101 to operate the disease management system 1101.

A disease management system 1101 may have one or more power and sleep modes to help regulate power usage. For example, a disease management system 1101 may have a sleep mode. The sleep mode may be a very low power mode with minimal functions, such as the RTC (or real time clock) and alarms to wake the system and take a temperature measurement of the system, or the like. In another example, a disease management system 1101 may include a measure temperature mode which may correspond to a low power mode with reduced functions. The measure temperature mode may be triggered by the RTC where the system is configured to take a temperature measurement, save the value, and return the system to a sleep mode. In another example, a disease management system 1101 may include a wake up mode. The wake up mode may be triggered by an NFC device and allow the system to pair with an external device with, for example, Bluetooth. If a pairing event does not occur, the system may return to sleep mode. In another example, a disease management system 1101 may include a pairing mode. The pairing mode may be triggered by an NFC device. When a controlling application is recognized, the system may proceed to pair with the application and set the system to an on condition and communicate to the cloud or other external device to establish initial data movement. In another example, a disease management system 1101 may include a rest mode where the system is configured to enter a lower power mode between measurements. In another example, a disease management system 1101 may include a data acquisition mode where the system is configured to enter a medium power mode where data acquisition takes place. In another example, a disease management system 1101 may include a parameter calculation mode where the system is configured to enter a medium power mode where parameter calculations, such as a blood glucose calculations, are performed and data is communicated to an external device and/or the cloud. In another example, a disease management system 1101 may include a pump mode where the system is configured to enter a higher power mode where the pump draws power to deliver medication to the patient.

A disease management system 1101 may include one or more connector test points 1146. The connecter test points may be configured to aid in programming, debugging, testing or other accessing of the disease management system 1101. In some examples, connector test points 1146 may include, for example, a GPIO spare, UART receiver or transmitter, the like or a combination thereof.

Figure 2:
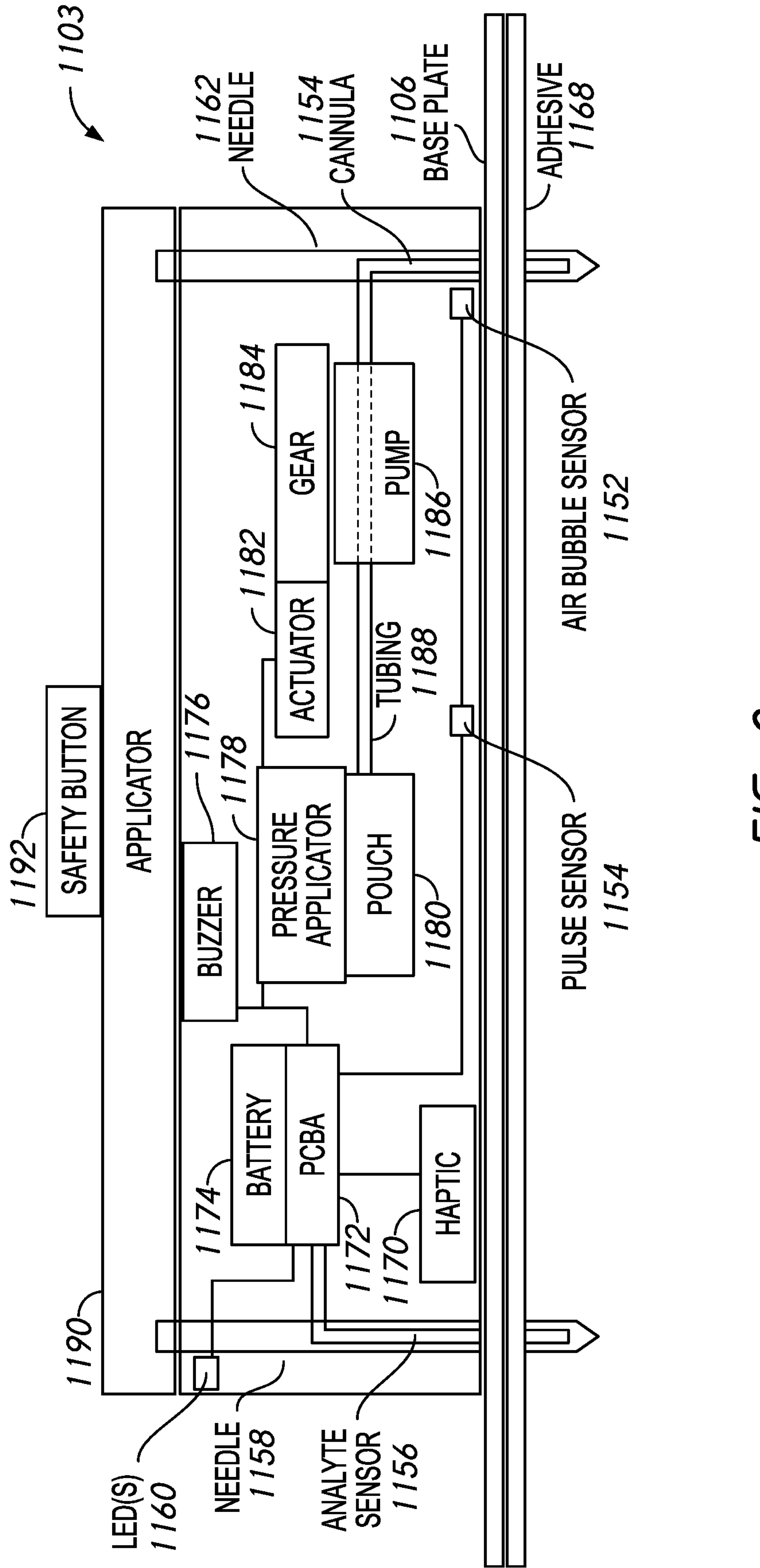
FIG. 2 illustrates an example implementation of a disease management system.

FIG. 2 illustrates an example implementation of a disease management system 1103 and applicator 1190 for applying a disease management system 1103 to a patient. Disease management system 1103 can include any one or more of the features discussed above with respect to the disease management system 1101 in addition to the features described below. In the illustrated example, an applicator 1190 may be configured to mate with the disease management system 1103. In some examples, an applicator 1190 may include a safety button 1192 for release or other interaction with the applicator 1190. In the illustrated example, a disease management system 1103 may include one or more LEDs 1160 that may be configured to output information using one or more of color, frequency, and length of display. In some examples, the disease management system 1103 may include a buzzer 1176, haptic actuator 1170, or other feedback mechanism, such as a speaker to output information to the patient, such as an alarm. In some examples, a disease management system 1103 may include a battery 1174, controller 1172. In some examples, a disease management system 1103 may include aspects of a medication administration system, such as a bladder 1180, a bladder pressure applicator 1178 to provide pressure on the bladder (such as a component of a pump), actuator 1182, pump gears 1184, and a pump 1186. In some examples, a disease management system 1103 may include one or more needles 1158 that may include one or more analyte sensors (such as a glucose sensor) 1156. In some examples, a disease management system 1103 may include one or more needles 1162 that may include one or more cannulas 1164 configured to administer medication to the patient. In some examples, a disease management system 1103 may include an air bubble sensor 1152 configured to detect the presence of air bubbles in the medication prior to delivery to the patient. In some examples, a glucose control system 1103 may include one or more physiological sensors 1154, such as a non-invasive physiological sensor including but not limited to a pulse sensor. In some examples, the disease management system 1103 may include a base plate 1106 and an adhesive layer 1168 below the base plate 1106 to provide adhesion of the disease management system 1103 to the patient's skin. As described below, a housing of the disease management system 1103 may consist of a combination of flexible and rigid material so as to both provide support for the components of the disease management system 1103 and allow conforming, at least in part, of the disease management system 1103 to the skin of the patient.

The adhesive layer 1168 may be configured to provide adhesion for a prolonged period. For example, the adhesive layer 1168 may be configured to adhere the disease management system 1103 to the skin of a patient for a period of 1 day, 3 days, 6 days, or more or fewer days or hours. In some examples, the adhesive layer may be configured to have an adhesive force sufficient to prevent accidental removal or movement of the disease management system 1103 during the intended period of use of the disease management system 1103. In some examples, the adhesive layer 1168 may be a single layer of adhesive across at least a portion of a surface the disease management system 1103 that is configured to interface with the patient. In some examples, the adhesive layer 1168 may include a plurality of adhesive areas on a surface of the disease management system 1103 that is configured to interface with the patient. In some examples, the adhesive layer 1168 may be configured to be breathable, adhere to the patient's skin after wetting by humidity or liquids such as tap water, saltwater, and chlorinated water. A thickness of the adhesive may be, for example, in a range of 0.1 to 0.5 mm or in a range of more or less thickness.

In some examples, a needle 1158, 1162 may be inserted at different depths based on a patient age, weight, or other parameter. For example, a depth of insertion of a medication cannula may be approximately 3 mm for 7 to 12 year olds. In another example, a depth of insertion of a medication cannula may be approximately 4 mm for 13 year olds and older. In another example, a depth of insertion of a medication needle may be approximately 4 to 4.5 mm for 7 to 12 year olds. In another example, a depth of insertion of a medication needle may be approximately 5 to 5.5 mm for 13 year olds and older. In another example, a depth of insertion of an analyte sensor may be approximately 3 mm for 7 to 12 year olds. In another example, a depth of insertion of an analyte sensor may be approximately 4 mm for 13 year olds and older. In another example, a depth of insertion for a needle associated with an analyte sensor may be approximately 4 to 4.5 mm for 7 to 12 year olds. In another example, a depth of insertion for a needle associated with an analyte sensor may be approximately 5 to 5.5 mm for 13 year olds and older. However, other values or ranges for any of the inserted components are also possible.

In some examples, an analyte sensor 1156, such as illustrated in FIG. 2, can include a micro-electrochemical cell configured to at least partially implantable into the tissue of the patient. The micro-electrochemical cell may include one or more sensor components enclosed at least in part in a permeable cell. The permeable cell may include one or more permeable portions configured to allow passage of analyte containing fluid from the surrounding tissue of the patient to a portion of the permeable cell containing the one or more sensor components. The one or more sensor components may be configured to measure at least one analyte, such as glucose or other analyte present at the tissue site of the patient.

Figure 3:
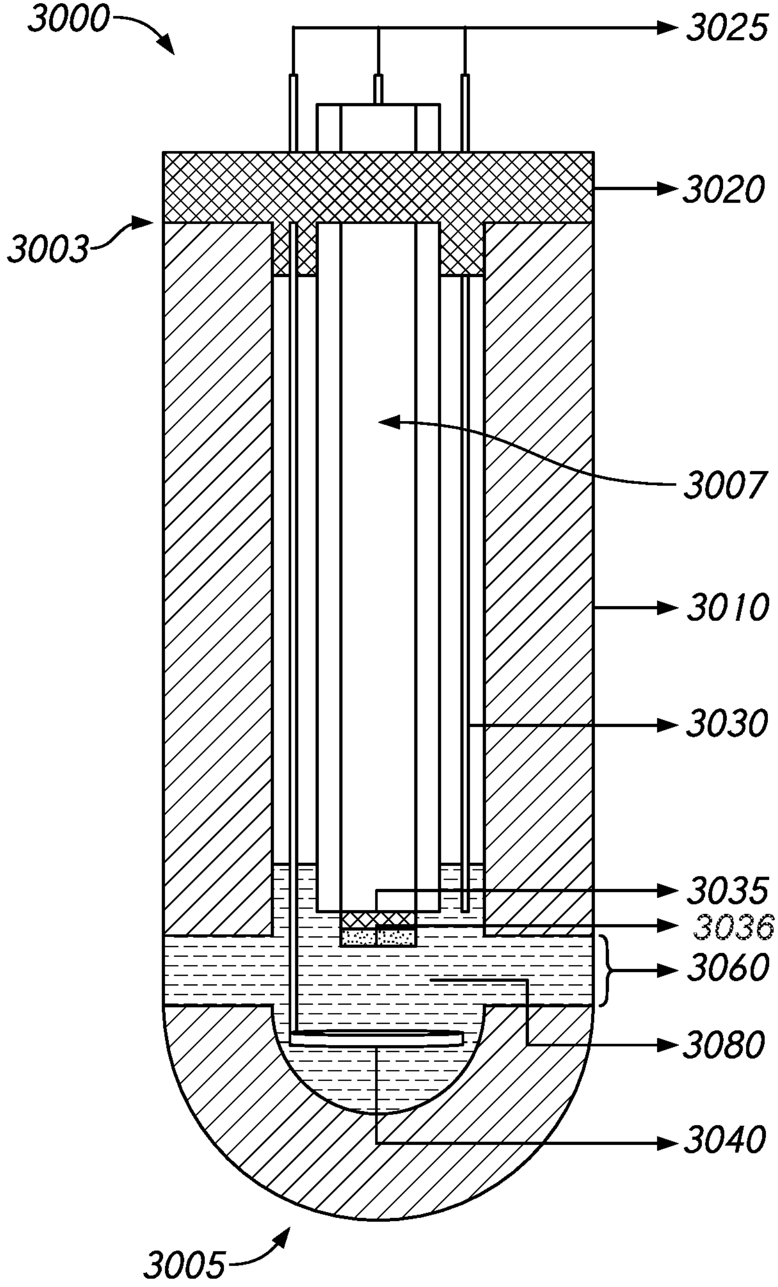
FIG. 3. Illustrates an example of an implantable micro-electrochemical cell.

FIG. 3 illustrates an example of an implantable micro-electrochemical cell 3000. The implantable micro-electrochemical cell may be implanted at least in part under the skin of the human body. The implantable micro-electrochemical cell can vary in depth of which it is implanted under the skin. For example, the implanted micro-electrochemical cell can be anywhere between up to and including 100% implanted underneath the skin. In some examples, the cell 3000 may be implanted so that at least a permeable sidewall portion 3060 may be implanted below the skin. In some examples, the cell 3000 may be implanted at a depth such that the permeable sidewall portion 3060 is in contact with bodily fluid containing analytes. In some instances, the implantable micro-electrochemical cell 3000 may be injected or inserted into the human body using a needle, such as described above with reference to FIG. 2, and connect to a device, such as a combined glucose sensor and insulin pump, that is located outside of the human body. In some example, one or more elements or substances inside the implantable micro-electrochemical cell 3000 may be protected from the outside. The implantable micro-electrochemical cell 3000 is configured to prevent contact of at least some of the interior components of the cell with portions of the tissue of the patient. In some examples, the cell 3000 may include a smooth outer surface. Advantageously, the smooth outer surface of the cell may protect tissue surrounding the outer surface of the cell 3000 from being irritated or injured from contact with the cell 3000. In some examples, the smooth outer surface may be made of, for example, silicones, polyethylene, polyimide, or the like. Furthermore, the longevity of the cell 3000 may be enhanced from reduced friction or other contact with tissue of the patient. In some examples, the cell 300 may be coated with a material to enhance biocompatibility upon implantation of the cell.

The implantable micro-electrochemical cell may include a permeable cell. The permeable cell may include a component that is at least partially closed to outside material. The geometry of the permeable cell may include a three dimensional shape having at least one smooth surface, such as a cuboid, a pyramid, a cylinder, or other object with at least one flat or curvilinear geometric shape or side. In some examples, the permeable cell shape may include a container portion 3010. The container portion 3010 may be tubular shape, such as illustrated in FIG. 3. A tubular shape for the permeable cell may provide greater surface area for the sensors compared to a flat surface. Additionally, a tubular shape may be easier to manufacture than a different shape, for example rectangular. Furthermore, a tubular shape may ease implantation of the permeable cell, such that a tubular shape may increase comfortability of the patient and/or a tubular shape may achieve a greater implantation depth than a shallower shape.

The permeable cell may be at least partially composed of a biocompatible material, such as a biocompatible plastic or the like. For example, the permeable cell may include at least one layer of a polyamide, other polymer, or the like. In some examples, the tube 3010 may have a length between approximately 3 mm to approximately 8 mm, such as 5 mm, an outer diameter between approximately 100 micrometers to approximately 500 micrometers, such as 300 mm, and an inner diameter between approximately 150 micrometers to approximately 450 micrometers, such as 250 mm. However, the cell may have smaller or larger dimensions. In some examples, preferably, the tube 3010 may have a length of approximately 5 mm. In some examples, preferably, the tube 3010 may have an outer diameter of approximately 300 micrometers. In some examples, preferably, the tube 3010 may have an inner diameter of approximately 250 micrometers. Advantageously the diameter of the cell may be sufficiently small so as to reduce the likelihood of a painful insertion or implantation of the micro-electrochemical cell in the tissue of the patient. Additionally, in some cases, the diameter of the cell may be sufficiently small to reduce damage or injury caused by the implantation of the cell. Furthermore, the overall size of the cell 3000 may be designed or sized to simplify the implantation procedure, such that the need for bulkier, less user friendly, tools may be minimized or eliminated.

The permeable cell may have at least one open end 3003 and a closed end 3005. The permeable cell may be sealed at the open end 3003 by a seal 3020. The seal 3020 may be used to close off the open end 3003 of the permeable cell or tube 3010 to prevent elements of the tube and substances within the tube from being misplaced. Additionally, the seal 3020 may be configured to include at least one electrical feedthrough to allow for electrode leads to pass through the seal and make an electrical connection with components of the at least one analyte sensor within the permeable cell. The electrode leads 3025 may then be configured to connect to one or more electrical components of a connected device, such as a combination insulin pump and analyte sensor and/or disease management device described with reference to FIG. 2. In some examples, the electrical feedthrough may at least partially not be implanted in the patient. This may provide easy access to the electrode without having to remove the permeable cell.

The open end 3003 may be located at the top portion of the permeable cell 3010. The closed end 3005 may be located at the bottom portion of the permeable cell 3010. In some examples, the open end 3003 may be positioned outside of the patient's body. In some examples, the closed end 3005 may be positioned inside of the patient's body. The open end 3003 positioned outside of the patient's body can provide a user access to the internal compartment of the permeable cell 3010 without have to remove the permeable cell 3010 from the patient's body. This can minimize the number of times the cell 3010 may be implanted and/or reimplanted after the initial implantation of the cell 3010. Additionally, the open end 3003 positioned outside of the patient's body and the closed end 3005 positioned inside of the patient's body can help to ensure that the internal elements of the permeable cell 3010 remain inside the permeable cell 3010.

In some examples, the closed end 3005 may be curved. This can increase the comfortability of the patient. For example, a curved closed end 3005 can help to ensure no sharp edges come in contact with the tissue site. This may minimize the irritation that the tissue site may experience.

An implantable micro-electrochemical cell 3000 may include one or more physiological sensors, including but not limited to an analyte sensor 3007. Furthermore, in some examples, the at least one electrode may include a non-electrochemical electrode or other sensor configured to measure a physiological parameter of a patient (e.g., optical sensor). An analyte sensor 3007 may include some combination of electrodes connected to one or more electrode leads 3025. For example, an analyte sensor 3007 may include at least one electrode, such as at least one reference electrode 3030, at least one counter electrode 3040, and/or at least one sensor electrode 3035.

An analyte sensor 3007 may include one or more sensor electrodes. U.S. Provisional Application No. 63/263,277, filed Oct. 29, 2022, is herein incorporated by reference in its entirety. The one or more sensor electrodes may be used to measure the presence and/or amount of the analyte within the bodily fluid. In some examples, the one or more sensor electrodes may include nanomaterials, polymers and/or polymeric composites such as chitosan, cellulose, and conducting polymers. In some examples, the one or more sensor electrodes may be rectangular in shape. In other examples, the one or more sensor electrodes may be cylindrical, conical, triangular, etc. in shape. The one or more sensor electrodes may have a thickness between approximately 10 micrometers to 50 micrometers. In some examples, the one or more sensor electrodes may be located within the internal compartment of the permeable cell 3010. The one or more sensor electrodes may be positioned in the center of the cell 3010. This may increase the ability for the one or more sensor electrodes to measure analytes at the tissue site by allowing the bodily fluid to come in contact with all sides of the sensor electrodes.

A sensor electrode 3035 may be configured to measure one or more analytes at the tissue site of the patient. For example, a sensor electrode may be configured to measure glucose, insulin, and/or other analytes. The one or more analytes may, in some examples, be in fluid 3060 within the cell 3000. In some examples, the sensor electrode 3035 may contain an insulting layer with a thickness of between approximately 10 micrometers to approximately 20 micrometers, such as 15 mm. The sensor electrode 3035 may have a tip 3036 that is modified with a suitable sensing element (e.g., an enzyme or the like). In some examples, preferably, the insulating layer may have a thickness of approximately 15 micrometers. The sensor electrode may have a diameter of approximately 80 micrometers to 120 micrometers. In some examples, the sensor electrode may have a diameter of approximately 100 micrometers.

An analyte sensor, such as a glucose sensor, is an amperometric electrochemical biosensor generating a current from the electrochemical reaction between an analyte, such as glucose and a glucose oxidase layer on working electrode (WE). An analyte sensor such as those described above can include some combination of electrodes, including a reference electrode, counter electrode, and working electrode. In general, the reference electrode (RE) eliminates the potential arising from a solution medium. In general, the counter electrode (CE) acts as a reference half-cell to supply the required current for the electrochemical reaction, whereas the WE acts as a sensing half-cell to produce current. The sensor system described herein may include at least two electrodes—the working electrode and the reference electrode.

In some aspects, the working electrode and/or the reference electrode may comprise one or more metals. In some further aspects, the working electrode and/or the reference electrode may comprise platinum (Pt), gold (Au), silver (Ag), rhodium (Rh), iridium (Ir), or combinations thereof.

In one aspect, the working electrode may comprise Pt. In some aspects, the working electrode may comprise both Pt and Au. In another aspect, the working electrode comprises both Pt and Ir. In some aspects, the working electrode may comprise two different metal layers. In some aspects, the bottom metal layer of a working electrode may be Au and the top metal layer of the working electrode may be Pt. In some aspects, the bottom metal layer of a working electrode may be Ag and the top metal layer of the working electrode may be Pt. In some aspects, the bottom metal layer of a working electrode may be Pt and the top metal layer of the working electrode may be Au or Ag. In some aspects, the thickness of the bottom metal layer may be about 2 μm, about 2.5 nm, about 3 nm, about 3.5 nm, about 4 μm, or any other thickness. In some aspects, the thickness of the top metal layer may be about 50 Å, about 70 Å, about 90 Å, about 100 Å, about 120 Å, about 150 Å, or any other thickness. In some aspects, the thickness of the top metal layer may be much less than the thickness of the bottom metal layer. The ratio of the thickness of the top metal layer to the thickness of the bottom metal layer may be less than about 1/500, 1/300, 1/100, or less than any other ratio.

An analyte sensor 3007 may include one or more reference electrodes. The one or more reference electrodes may include Ag/AgCl, or the like. In some examples, the reference electrode 3030 may be rectangular in shape. In other examples, the one or more reference electrodes may be cylindrical, conical, triangular, etc. in shape. The one or more reference electrodes may be located within the internal compartment of the cell 3010. The reference electrode 3030 of the analyte sensor may have a diameter of approximately 10 micrometers to 30 micrometers. In some examples, the diameter of the analyte sensor may be approximately 20 micrometers. In some examples, a plurality of electrodes may be contained within the cell 3000. The reference electrode 3030 may have an accurately maintained potential to be used as a reference for other sensor electrodes within the cell.

In one embodiment, the reference electrode may comprise silver and silver chloride (Ag/AgCl), Hydrogen, SCE, or the like. In some aspects, the thickness of the metal layer in the reference electrode may be about 2 μm, about 2.5 μm, about 3 μm, about 3.5 μm, about 4 μm, or any other thickness. This can advantageously affect the size and shape of the cell. For example, the thinner the metal layer in the reference electrode, the smaller the overall size of the cell may be.

In some aspects, the thickness of the reference electrode 520 may be about 2 μm, about 2.5 μm, about 3 μm, about 3.5 μm, about 4 μm, and or other thickness. In some aspects, the reference electrode 520 may comprise silver. In some aspects, the reference electrode 520 may comprise a bottom metal layer and a top metal layer. In some aspects, the bottom metal layer may be about 2 μm, about 2.5 μm, about 3 μm, about 3.5 μm, about 4 μm, and or other thickness. In some aspects, the reference electrode 520 may comprise a top metal later. The top metal layer may be about 50 Å, about 70 Å, about 90 Å, about 100 Å, about 120 Å, about 150 Å, or any other thickness. In some aspects, the thickness of the working electrode 510 and the reference electrode 520 may be similar.

An analyte sensor 3007 may include one or more counter electrodes. The one or more counter electrodes may be rectangular in shape. In other examples, the one or more counter electrodes may be cylindrical, conical, triangular, etc. in shape. The one or more counter electrodes may be located within the internal compartment of the cell 3010. The counter electrode 3040 may have a diameter of approximately 10 micrometers to 40 micrometers. In some examples, the counter electrode may have a diameter of approximately 30 micrometers. In some examples the counter electrode 3040 may consist of platinum or the like. The one or more counter electrodes can be an inert conductor.

In some aspects, the device may further comprise a counter electrode. The counter electrode may comprise one or more metals described herein. In one embodiment, the counter electrode comprises Au. In another embodiment, the counter electrode comprises Pt. In another embodiment, the counter electrode comprises carbon. In some aspects, the thickness of the metal layer in the counter electrode may be about 2 μm, about 2.5 μm, about 3 μm, about 3.5 μm, about 4 μm, and or other thickness. This can advantageously affect the size and shape of the cell. For example, the thinner the metal layer in the counter electrode, the smaller the overall size of the cell may be.

The at least one electrode lead 3025 may be sealed, such that an inner side of the tube is isolated from the at least one electrode leads 3025. In some examples, the at least one electrode lead 3025 may be sealed with a polymer resin or the like.

The implantable micro-electrochemical cell 3000 may include at least one porous interface 3060. The at least one porous surface 3060 may include at least a portion of the permeable cell that is configured to allow at least some transmission of analytes at the implantation site of the cell to access an interior portion of the cell 3000 and make contact with an analyte sensor inside the interior portion. In some examples, a porous interface 3060 may be a mesh or other permeable membrane. In some examples, the porous interface 3060 may be generated by laser drilling the tube 3010 so as to create a plurality of holes or pores in the surface of the tube 3010. In other examples, the tube 3010 may be formed with a mold and polymer resin to encompass the porous interface 3060. The diameter of pores or holes in the porous interface 3060 may range between 10-50 micrometers or more or less than that range. In some examples, the porous interface 3060 may be adequately sizable enough to allow for diffusion of glucose into a fluid medium 3080 within the cell with minimal resistance, which may increase the ability for fresh glucose or other analytes to enter the cell 3000 from surrounding tissue of the patient when the cell 3000 is implanted.

The sensor electrode 3050 may be configured to measure analytes within a fluid medium 3080. The fluid medium 3080 may be provided into the interior of the permeable cell at the site of the porous interface. The fluid medium 3080 may be configured to act as an interface and provide fluid communication with bodily fluid or analytes entering the permeable cell through the porous interface and at least a portion of the at least one analyte sensor. some examples, the fluid medium 3080 may contain a cross-linked water absorbing polymer matrix. For example, the cross-linked water absorbing polymer matrix may include a hydrogel formed by cross-linking polyethylene glycol diglycidyl ether and polyethylene glycol diamine.

Example Analyte Sensor Configuration

Figure 4:
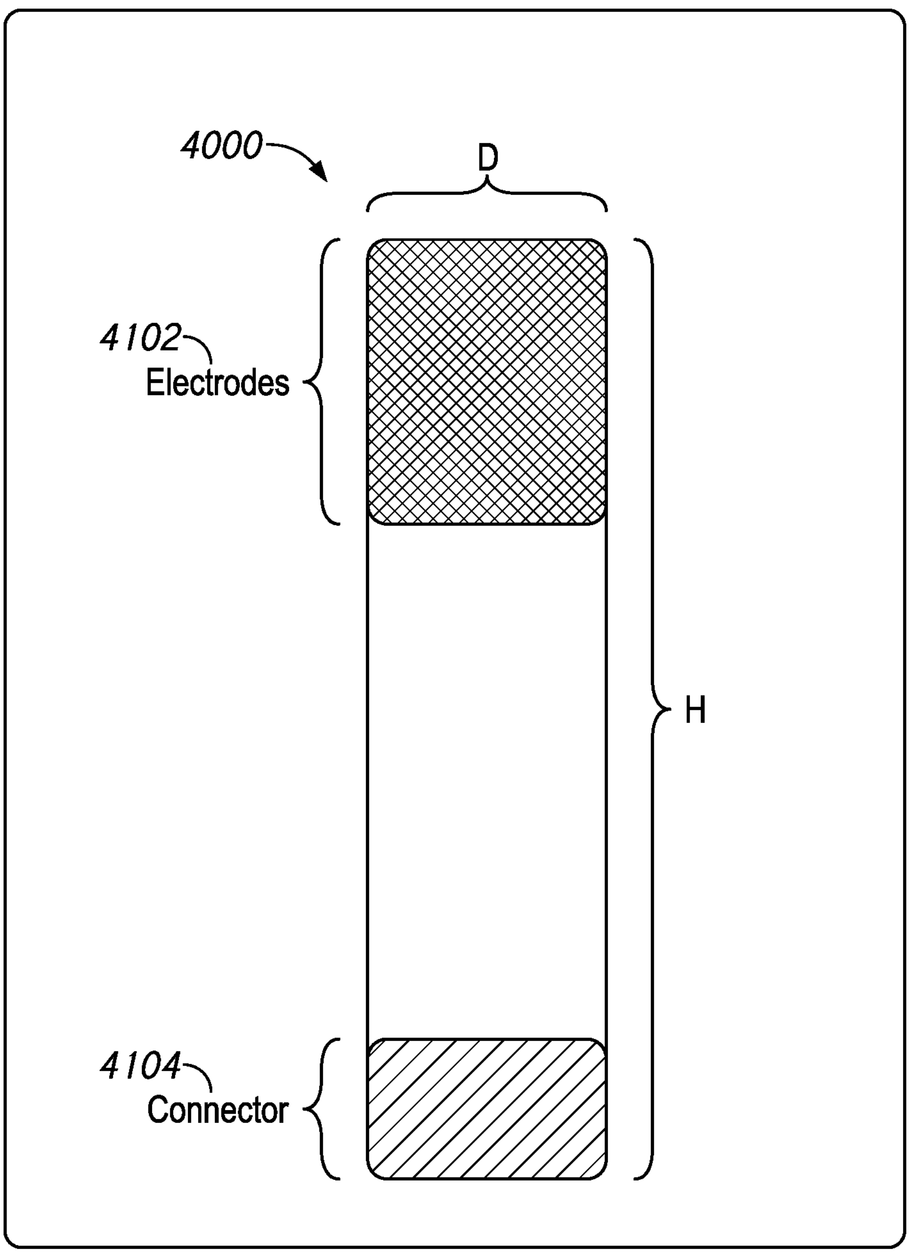
FIG. 4 illustrates an example layout of an example analyte sensor system.

FIG. 4 illustrates an example configuration of an analyte sensor system 4000 that may be used in within the cell 3000 referenced in FIG. 3. An analyte sensor system 4000 may include some combination of electrodes 4102 and connector(s) 4104. The electrodes, at least in part, may be implanted into a tissue of a patient such that interstitial fluid containing one or more analytes comes into contact with the one or more electrodes 4102. This can allow for an accurate measurement of the interstitial fluid and/or collection of data. The connector(s) 4104 may be disposed outside the human body and/or may be in electrical connection with a disease management system, such as described above. The connector(s) 4104 may allow for continuous and real-time monitoring of the analytes measured within the interstitial fluid. In some examples, a width, D, of the sensor system 4000 may be approximately 1 mm or more or fewer mm. In some examples, a height, H, of the sensor system 4000 may be approximately 10 mm, 20 mm, or more or fewer mm. At least part of the sensor system 4000 may be configured to be formed into a non-flat configuration, such as a cylindrical or otherwise curved shape. In some examples, at least a portion of the electrodes 4102 may be curved along a vertical or horizontal axis. This can advantageously contribute to the size and/or shape of the cell. For example, a non-flat configuration of the sensor system 4000 may fit into a smaller space, which can minimize any negative implantation effects due to the size and/or shape of the implantable cell.

Figure 5:
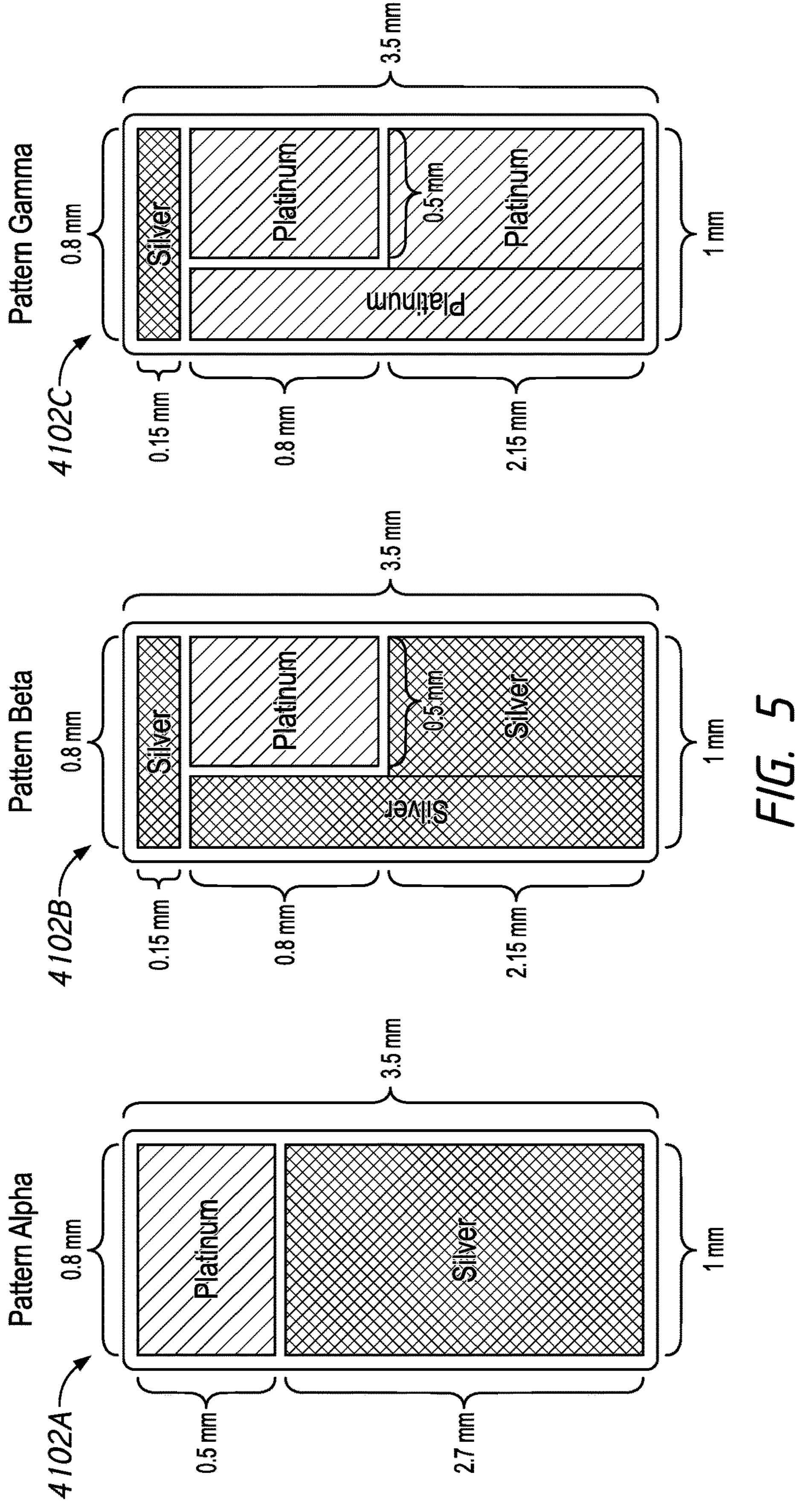
FIG. 5 illustrates example layout of electrodes in an example analyte sensor system.

The electrodes 4102 may have a layout or pattern in one or more configurations. FIG. 5 illustrates some example configurations 4102A, 4102B, 4102C of electrodes 4102. In a first configuration 4102A, an analyte sensor includes a combination of two electrodes. In the configuration of two electrodes, a sensor electrode may include platinum and a reference electrode may include silver. The reference electrode may be larger than the sensor electrode. In a two electrode configuration, the electrodes may be patterned onto a flexible or semi-flexible substrate and configured to be wrapped around or curved around a cylindrical or other shape such that the reference and sensor electrodes face outwards towards interstitial fluid.

In a second 4102B and third 4102C configuration, an analyte sensor may include three electrodes. In a three electrode configuration, the analyte sensor can include a sensor electrode, reference electrode, and counter electrode. In a second configuration 4102B, the reference electrode and the counter electrode may be silver and the sensor electrode may be platinum. In a third configuration 4102C, the reference electrode may be silver and the counter electrode and sensor electrode may be platinum. It is of note that use of a metal other than silver for, for example, a counter electrode, may result in microscopic bubbles of air, which can cause problems in measurements. In the second and third configuration, the electrodes may be patterned onto a flexible or semi-flexible substrate and configured to be wrapped around or curved around a cylindrical or other shape such that the electrodes either face outwards or face inwards. The electrodes can measure the bodily fluids containing analytes when facing either direction. With a pattern of electrodes facing towards the outside, the electrodes may have more access to bodily fluids containing analytes. However, while the implantable cell and/or electrodes may include a biocompatible coating to increase biocompatibility of the cell, the body can attack the electrodes and the layers of chemistry associated with the sensor due to an immune response. With a pattern of electrodes facing towards the inside, the electrodes may continue to have access towards bodily fluids and the configuration may be placed in an electrochemical cell, such as described herein and illustrated, for example, in FIG. 6. Advantageously, the use of an interior facing configuration in an electrochemical cell using a hydrogel or other medium to transmit interstitial fluids and/or analytes to the electrodes of the sensor can allow use of either a platinum or silver counter electrode with reduced issues (such as the presence of microscopic bubbles) than if the electrodes of the sensor system were in direct contact with tissue.

Figure 6:
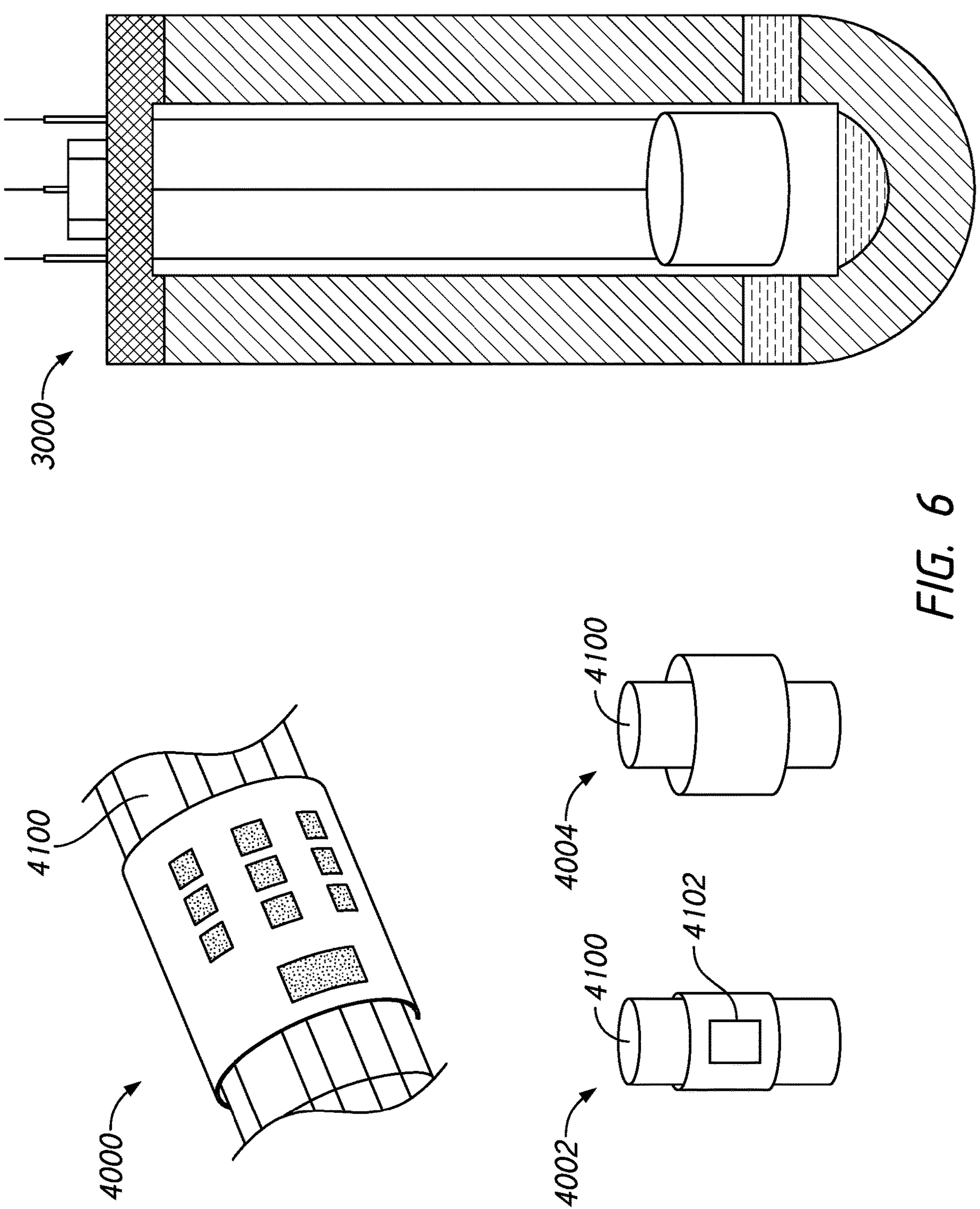
FIG. 6 illustrates an example embodiment of an analyte sensor that may be included in an implantable electrochemical cell.

FIG. 6 illustrates example configurations of an analyte sensor system, such as described above. The configurations illustrated in FIG. 6 may include a cylindrical or curved configuration of an analyte sensor system 4000. In some examples, at least a portion of the sensor system 4000 may be curved or shaped around a core 4100. In some examples, such as shown in configuration 4002, the core 4100 may provide shape, structure, and/or stability for the sensor system 4000. In providing shape, structure, and/or stability for the sensor system 4000, the core 4100 may allow the sensor system to more accurately measure the analytes within the bodily fluid. In some examples, such as shown in configuration 4004, some or all of the sensor system 4000 may be freely standing from the core 4100. In some examples one or more electrodes 4102 may be positioned on an outer surface of the sensor system 4000, such as shown in configuration 4002 and in some examples, one or more electrodes 4102 may be positioned on an inner surface (such as facing a core 4100 or center portion of the sensor system 4000) such that analytes in a medium surrounding the sensor system 4000 may be measured on the interior portion of the sensor system 4000. In some examples, a curved analyte sensor system 4000 may be configured to measure analytes in the interior of an electrochemical cell 3000, such as described above with reference to FIG. 3. Electrodes 4102 of the sensor system may be configured to point towards an interior of the cell and analytes may come into contact with the electrodes through the hydrogel or other medium in the interior of the electrochemical cell. This configuration may protect the electrodes from being attacked by the immune response produced upon implantation of the cell.

Terminology

Unless defined otherwise, all technical and scientific terms used herein have the same meaning as is commonly understood by one of ordinary skill in the art. The use of the term "including" as well as other forms, such as "include", "includes," and "included," is not limiting. The use of the term "having" as well as other forms, such as "have", "has," and "had," is not limiting. The terms "comprising," "including," "having," and the like are synonymous and are used inclusively, in an open-ended fashion, and do not exclude additional elements, features, acts, operations, and so forth. That is, the above terms are to be interpreted synonymously with the phrases "having at least" or "including at least." For example, when used in the context of a process, the term "comprising" means that the process includes at least the recited steps, but may include additional steps. When used in the context of a device, the term "comprising" means that the device includes at least the recited features or components, but may also include additional features or components. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount.

The term "and/or" as used herein has its broadest least limiting meaning which is the disclosure includes A alone, B alone, both A and B together, or A or B alternatively, but does not require both A and B or require one of A or one of B. As used herein, the phrase "at least one of" A, B, "and" C should be construed to mean a logical A or B or C, using a non-exclusive logical or.

The term "temperature independent" as used herein, means that the reading or measurement of the glucose level by the glucose monitoring device or the response of the glucose sensor is not affect or not substantially affected by the change of temperature. In other words, the sensor is insensitive the change of temperature (e.g., change of body temperature as a result of physiological conditions such as hypothermia and hyperpyrexia). In some embodiments, the temperature independent property of the glucose monitoring device is maintained within the operating temperature range of the device (e.g., from about 30° C. to about 45° C., from about 33° C. to about 43° C., from about 35° C. to about 41° C., or from about 36° C. to about 40° C. In some embodiments, the change of temperature (per ° C.) results in less than 5%, 4%, 3%, 2%, 1%, 0.5%, 0.1% or 0.01% change in the response of the sensor, or the measurement/reading provided by the device, when all the other parameters remain the same (e.g., the glucose concentration is constant).

Any methods disclosed herein need not be performed in the order recited. The methods disclosed herein include certain actions taken by a practitioner; however, they can also include any third-party instruction of those actions, either expressly or by implication.

Conditional language used herein, such as, among others, "can," "could," "might," "may," "e.g.," and the like, unless specifically stated otherwise, or otherwise understood within the context as used, is generally intended to convey that certain, certain features, elements and/or steps are optional. Thus, such conditional language is not generally intended to imply that features, elements and/or steps are in any way required or that one or more implementations necessarily include logic for deciding, with or without other input or prompting, whether these features, elements and/or steps are included or are to be always performed. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain implementations require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain implementations, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

Any methods disclosed herein need not be performed in the order recited. The methods disclosed herein include certain actions taken by a practitioner; however, they can also include any third-party instruction of those actions, either expressly or by implication.

The methods and tasks described herein may be performed and fully automated by a computer system. The computer system may, in some cases, include multiple distinct computers or computing devices (for example, physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (for example, solid state storage devices, disk drives, etc.). The various functions disclosed herein may be embodied in such program instructions, and/or may be implemented in application-specific circuitry (for example, ASICs or FPGAs) of the computer system. Where the computer system includes multiple computing devices, these devices may, but need not, be co-located. The results of the disclosed methods and tasks may be persistently stored by transforming physical storage devices, such as solid state memory chips and/or magnetic disks, into a different state. The computer system may be a cloud-based computing system whose processing resources are shared by multiple distinct business entities or other users.

While the above detailed description has shown, described, and pointed out novel features, it can be understood that various omissions, substitutions, and changes in the form and details of the devices or algorithms illustrated can be made without departing from the spirit of the disclosure. As can be recognized, certain portions of the description herein can be embodied within a form that does not provide all of the features and benefits set forth herein, as some features can be used or practiced separately from others. The scope of certain implementations disclosed herein is indicated by the appended claims rather than by the foregoing description. All changes which come within the meaning and range of equivalency of the claims are to be embraced within their scope.

What is claimed is:

1. An implantable electrochemical cell for facilitating physiological measurement at a tissue site of a patient, comprising:

- a container portion configured to be at least partially implanted in the tissue site of the patient, the container portion comprising:
  - an open end;
  - a closed end configured to be implanted in the patient;
  - at least one sidewall at least partially implanted in the patient, wherein the at least one sidewall comprises at least one porous interface configured to allow one or more analytes, from bodily fluid of the patient at the tissue site, to enter into an interior volume of the container portion; and
  - a fluid medium occupying the interior volume of the container portion, the interior volume defined at least in part by the closed end and the at least one sidewall;
- an analyte sensor configured to measure at least one analyte from the one or more analytes in the fluid medium, the analyte sensor extending from the open end towards the closed end and into the interior volume, wherein the analyte sensor comprises:
  - a sensor electrode comprising an enzyme,
  - a counter electrode, and
  - a reference electrode, each of the sensor electrode, counter electrode, and reference electrode immersed in and spaced apart within the fluid medium, the fluid medium configured to allow diffusion of the at least one analyte from bodily fluid of the tissue site to the analyte sensor;

a seal configured to close the open end, the seal comprising a feedthrough; and at least one electrical connection extending through the feedthrough from the analyte sensor to one or more hardware processors not implanted in the patient.

2. The implantable electrochemical cell of claim 1, wherein the tissue site of the patient is at least one of:

an abdomen of the patient; or an arm of the patient.

3. The implantable electrochemical cell of claim 1, wherein the implantable electrochemical cell operates in connection with a disease management system.

4. The implantable electrochemical cell of claim 1, wherein the implantable electrochemical cell is tubular in shape, and the closed end comprises a rounded bottom portion.

5. The implantable electrochemical cell of claim 1, wherein the fluid medium comprises a cross-linked water absorbing polymer matrix.

6. The implantable electrochemical cell of claim 1, wherein a diameter of the at least one porous interface ranges between 10-50 micrometers.

7. The implantable electrochemical cell of claim 1, wherein the analyte sensor includes an insulting layer and a tip modified with a suitable sensing element configured to be immersed in the fluid medium.

8. The implantable electrochemical cell of claim 7, wherein the suitable sensing element comprises an enzyme.

9. The implantable electrochemical cell of claim 1, wherein the at least one electrical connection is complimented by the reference electrode or the counter electrode configured to be immersed in the fluid medium.

10. The implantable electrochemical cell of claim 1, wherein the at least one electrical connection is sealed with a polymer resin such that an inner side of the implantable electrochemical cell is at least partially isolated from the at least one electrical connection.

11. The implantable electrochemical cell of claim 1, wherein the analyte sensor comprises at least three electrodes patterned onto a flexible substrate, wherein the analyte sensor is configured to wrap around a cylindrical structure within the implantable electrochemical cell.

12. The implantable electrochemical cell of claim 11, wherein the at least three electrodes of the analyte sensor are configured to face an outward direction from a center of the cylindrical structure.

13. The implantable electrochemical cell of claim 11, wherein the at least three electrodes of the analyte sensor are configured to face an inward direction from a center of the cylindrical structure.

14. The implantable electrochemical cell of claim 1, wherein the at least one analyte comprises glucose.

15. A disease management system, the disease management system comprising:

an electrochemical cell configured to facilitate physiological measurement at a tissue site of a patient, the electrochemical cell comprising:

a container portion configured to be at least partially implanted in the tissue site of the patient the container portion comprising:

an open end;

a closed end configured to be implanted in the patient;

at least one sidewall at least partially implanted in the patient; and a semi-permeable portion comprising:

at least one porous interface positioned in the at least one sidewall, the at least one porous interface configured to allow one or more analytes, from bodily fluid of the patient at the tissue site, to enter into an interior volume of the container portion; and a fluid medium occupying the interior volume of the container portion, the interior volume defined at least in part by the closed end and the at least one sidewall; and an analyte sensor configured to measure at least one analyte from the at least one or more analytes in the fluid medium, the analyte sensor extending from the open end towards the closed end and into the interior volume, wherein the analyte sensor comprises:

a sensor electrode comprising an enzyme, a counter electrode, and a reference electrode, each of the sensor electrode, counter electrode, and reference electrode immersed in and spaced apart within the fluid medium, the semi-permeable portion configured to allow diffusion of the at least one analyte from bodily fluid of the tissue site to the analyte sensor;

a seal configured to close the open end, the seal comprising a feedthrough; and at least one electrical connection extending through the feedthrough; and at least one hardware processor connected to the at least one electrical connection of the electrochemical cell, the at least one hardware processor configured to process a plurality of data from the analyte sensor and output at least one measurement to a display.

16. The disease management system of claim 15, wherein the disease management system is configured to utilize the plurality of data to monitor or manage an insulin level of the patient.

17. The disease management system of claim 15, wherein the disease management system is an element of a minimally invasive device that manages delivery of at least one medication to the patient.

18. The disease management system of claim 15, wherein the semi-permeable portion of the electrochemical cell is configured to be at least partially implanted in the patient.

19. The disease management system of claim 15, wherein the at least one analyte comprises glucose.

* * * * *